(12) United States Patent
Danek

(10) Patent No.: US 12,156,547 B2
(45) Date of Patent: *Dec. 3, 2024

(54) ELECTRONIC DEVICE FOR PRODUCING AN AEROSOL FOR INHALATION BY A PERSON

(71) Applicant: QNOVIA, INC., Richmond, VA (US)

(72) Inventor: Mario Danek, Los Angeles, CA (US)

(73) Assignee: QNOVIA, INC., Richmond, VA (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/858,039

(22) Filed: Jul. 5, 2022

(65) Prior Publication Data

US 2022/0338534 A1    Oct. 27, 2022

Related U.S. Application Data

(63) Continuation of application No. 16/548,831, filed on Aug. 22, 2019, now abandoned.

(Continued)

(51) Int. Cl.
*A24F 7/02* (2006.01)
*B05B 17/00* (2006.01)

(52) U.S. Cl.
CPC ............ *A24F 7/02* (2013.01); *B05B 17/0646* (2013.01)

(58) Field of Classification Search
None
See application file for complete search history.

(56) References Cited

U.S. PATENT DOCUMENTS 5,322,075 A    6/1994 Deevi et al.
5,435,282 A    7/1995 Haber et al.
(Continued)

FOREIGN PATENT DOCUMENTS

CA        73714      12/1993
CN    206043434 U    3/2017
(Continued)

OTHER PUBLICATIONS

"Innokin Adept: Unboxing Experience" (Kai's Virgin Vapor), Jul. 27, 2021, retrieved from https://web.archive.org/web/20210727211502/https://www.kaisvirginvapor.com/pages/innokin-adept-unboxing-experience.

(Continued)

*Primary Examiner* — Phu H Nguyen
(74) *Attorney, Agent, or Firm* — TILLMAN WRIGHT, PLLC; Chad D. Tillman

(57) ABSTRACT

An electronic device for producing an aerosol for inhalation has a mouthpiece and an elongate housing. The mouthpiece attaches to an upper end of the housing. The housing contains a liquid container and a mesh assembly with mesh material that vibrates when actuated for aerosolizing liquid from the container. The mouthpiece covers the mesh assembly at the upper end of the housing, and the aerosol produced by the mesh assembly may be inhaled through the mouthpiece by a person. The housing contains circuitry and a power supply, preferably are located in a lower half of the housing, for actuating vibration of the mesh material. Electrical pathways connect the mesh assembly with the circuitry and power supply. The power supply may comprise one or more batteries located at the lower end of the housing. The aerosol is produced without smoldering of the liquid and without using a compressed gas.

10 Claims, 14 Drawing Sheets

Related U.S. Application Data

(60) Provisional application No. 62/721,310, filed on Aug. 22, 2018.

(56) References Cited

U.S. PATENT DOCUMENTS

| | | |
|---|---|---|
| 5,510,118 A | 4/1996 | Bosch et al. |
| 5,518,179 A | 5/1996 | Humberstone |
| 5,586,550 A | 12/1996 | Ivri et al. |
| 5,938,117 A | 8/1999 | Ivri |
| 5,970,974 A | 10/1999 | Van Der Linden et al. |
| 6,138,669 A | 10/2000 | Rocci, Jr. et al. |
| 6,196,218 B1 | 3/2001 | Voges |
| 6,293,474 B1 | 9/2001 | Helf et al. |
| 6,427,682 B1 | 8/2002 | Klimowicz et al. |
| 6,544,542 B1 | 4/2003 | Sonoke et al. |
| 6,748,944 B1 | 6/2004 | DellaVecchia et al. |
| 6,915,962 B2 | 7/2005 | Power et al. |
| 7,013,894 B2 | 3/2006 | McFarland |
| 7,243,648 B2 | 7/2007 | Yang et al. |
| 7,380,729 B2 | 6/2008 | Wendt et al. |
| 7,387,265 B2 | 6/2008 | Hess et al. |
| 7,458,372 B2 | 12/2008 | Feiner et al. |
| 7,470,547 B2 | 12/2008 | Tisone et al. |
| 7,712,466 B2 | 5/2010 | Addington |
| 7,726,306 B2 | 6/2010 | Addington |
| 7,771,642 B2 | 8/2010 | Power et al. |
| 7,832,410 B2 | 11/2010 | Hon |
| 7,861,943 B2 | 1/2011 | Feriani et al. |
| 7,883,031 B2 | 2/2011 | Collins, Jr. |
| 7,934,703 B2 | 5/2011 | Tomono et al. |
| 7,950,595 B2 | 5/2011 | Feriani et al. |
| 8,012,136 B2 | 9/2011 | Collins, Jr. et al. |
| 8,109,266 B2 | 2/2012 | Addington |
| 8,187,554 B2 | 5/2012 | Panagiotou |
| 8,261,739 B2 | 9/2012 | Harris et al. |
| 8,328,115 B2 | 12/2012 | Feriani et al. |
| 8,336,545 B2 | 12/2012 | Fink |
| 8,353,287 B1 | 1/2013 | Hollen et al. |
| 8,418,690 B2 | 4/2013 | Power et al. |
| 8,545,463 B2 | 10/2013 | Collins, Jr. et al. |
| 8,555,874 B2 | 10/2013 | Fink |
| 8,616,195 B2 | 12/2013 | Power |
| 8,684,980 B2 | 4/2014 | Hunter |
| D707,352 S | 6/2014 | Liu et al. |
| 8,794,742 B2 | 8/2014 | Yamaguchi |
| 8,888,548 B2 | 11/2014 | Yi |
| 8,888,925 B2 | 11/2014 | Sato et al. |
| 8,910,625 B2 | 12/2014 | Mullinger |
| 8,936,021 B2 | 1/2015 | Collins, Jr. |
| 9,022,027 B2 | 5/2015 | Addington |
| 9,061,303 B2 | 6/2015 | Waldner et al. |
| 9,168,556 B2 | 10/2015 | Pumm et al. |
| 9,215,895 B2 | 12/2015 | Bowen et al. |
| 9,220,294 B2 | 12/2015 | McCullough |
| 9,260,849 B2 | 2/2016 | Frey et al. |
| 9,339,838 B2 | 5/2016 | Moran |
| 9,352,108 B1 | 5/2016 | Reed et al. |
| 9,358,569 B2 | 6/2016 | Burt |
| 9,380,813 B2 | 7/2016 | McCullough |
| 9,439,455 B2 | 9/2016 | Alarcon |
| 9,533,323 B2 | 1/2017 | Sauzade |
| 9,539,589 B2 | 1/2017 | Araki |
| 9,539,604 B2 | 1/2017 | Wilkerson et al. |
| D779,719 S | 2/2017 | Qiu |
| 9,572,950 B2 | 2/2017 | Power et al. |
| 9,592,524 B2 | 3/2017 | Fritz et al. |
| 9,636,431 B2 | 5/2017 | Teeling et al. |
| 9,718,078 B1 | 8/2017 | Chau et al. |
| 9,744,319 B2 | 8/2017 | Denyer |
| 9,757,528 B2 | 9/2017 | Rubin |
| D799,110 S | 10/2017 | Qiu |
| 9,956,360 B2 | 5/2018 | Germinario |
| 9,962,507 B2 | 5/2018 | Germinario et al. |
| 10,029,053 B2 | 7/2018 | Casey et al. |
| 10,076,140 B2 | 9/2018 | Silvestrini |
| 10,080,736 B2 | 9/2018 | Kleidon |
| D830,538 S | 10/2018 | Guillermo et al. |
| D831,822 S | 10/2018 | Guillermo et al. |
| 10,137,261 B2 | 11/2018 | Knudsen |
| D846,796 S | 4/2019 | Pan |
| 10,292,436 B2 | 5/2019 | Cirillo |
| 10,300,228 B2 | 5/2019 | Minskoff |
| D853,632 S | 7/2019 | Qiu et al. |
| 10,334,888 B2 | 7/2019 | Cameron et al. |
| 10,349,674 B2 | 7/2019 | Sur |
| 10,349,676 B2 | 7/2019 | King et al. |
| 10,350,556 B2 | 7/2019 | Xiong |
| 10,412,997 B2 | 9/2019 | Cameron et al. |
| D863,670 S | 10/2019 | He et al. |
| D863,673 S | 10/2019 | Lai |
| 10,449,314 B2 | 10/2019 | Germinario et al. |
| 10,464,095 B2 | 11/2019 | Fritz et al. |
| D870,369 S | 12/2019 | Greenbaum et al. |
| D870,372 S | 12/2019 | Zhu |
| 10,525,220 B2 | 1/2020 | Hunter |
| 10,531,687 B2 | 1/2020 | Liu |
| 10,548,349 B2 | 2/2020 | Sur |
| 10,561,803 B2 | 2/2020 | Liu |
| 10,609,962 B2 | 4/2020 | Zhu |
| 10,617,834 B2 | 4/2020 | Gould |
| 10,632,267 B2 | 4/2020 | Howell |
| D885,655 S | 5/2020 | Ding |
| D885,656 S | 5/2020 | Clough et al. |
| 10,661,036 B2 | 5/2020 | McCullough |
| 10,667,559 B2 | 6/2020 | Bessant |
| 10,737,042 B2 | 8/2020 | Minskoff |
| 10,786,010 B2 | 9/2020 | Hubbard |
| 10,792,455 B2 | 10/2020 | Power et al. |
| 10,821,240 B2 | 11/2020 | McCullough |
| D904,678 S | 12/2020 | Wang et al. |
| D905,329 S | 12/2020 | Wang |
| 10,856,572 B2 | 12/2020 | Sur |
| 10,857,313 B2 | 12/2020 | Fink |
| 10,888,117 B2 | 1/2021 | Danek |
| D909,667 S | 2/2021 | Chen |
| D909,668 S | 2/2021 | Chen |
| D910,233 S | 2/2021 | Grimm et al. |
| 10,918,127 B2 | 2/2021 | Fuisz |
| 11,011,270 B2 | 5/2021 | Hunter et al. |
| 11,027,076 B2 | 6/2021 | Casey et al. |
| 11,027,077 B2 | 6/2021 | Porter et al. |
| 11,039,641 B2 | 6/2021 | Liu |
| 11,077,261 B2 | 8/2021 | Liu |
| 11,131,000 B1 | 9/2021 | Lahoud et al. |
| 11,156,766 B2 | 10/2021 | Novak et al. |
| 11,247,003 B2 | 2/2022 | Rubin |
| 11,253,885 B2 | 2/2022 | Paunescu |
| 11,254,979 B2 | 2/2022 | Saleh et al. |
| 11,260,416 B2 | 3/2022 | Wilkerson et al. |
| 11,274,352 B2 | 3/2022 | Lahoud et al. |
| 11,285,274 B2 | 3/2022 | Germinario et al. |
| 11,285,283 B2 | 3/2022 | Germinario et al. |
| 11,285,284 B2 | 3/2022 | Germinario et al. |
| 11,285,285 B2 | 3/2022 | Germinario et al. |
| 11,317,476 B2 | 4/2022 | Schmidt |
| 11,325,149 B2 | 5/2022 | Tan |
| 11,372,153 B2 | 6/2022 | Novak et al. |
| 11,376,380 B2 | 7/2022 | Biette |
| 11,445,574 B2 | 9/2022 | Cameron et al. |
| 11,458,267 B2 | 10/2022 | Hebrank |
| 11,460,631 B2 | 10/2022 | Novak et al. |
| 11,478,019 B2 | 10/2022 | Qiu |
| 11,517,039 B2 | 12/2022 | Cameron et al. |
| 11,517,685 B2 | 12/2022 | Danek |
| 11,529,476 B2 | 12/2022 | Hunter |
| 11,553,730 B2 | 1/2023 | Cameron et al. |
| 11,558,934 B2 | 1/2023 | Ouyang |
| 11,571,022 B2 | 2/2023 | Lahoud et al. |
| 11,589,610 B2 | 2/2023 | Lahoud et al. |
| 11,592,793 B2 | 2/2023 | Novak et al. |
| 11,602,165 B2 | 3/2023 | Lahoud et al. |
| 11,614,720 B2 | 3/2023 | Novak et al. |
| 11,653,152 B1 | 5/2023 | Lahoud |
| 11,654,448 B2 | 5/2023 | Aherne et al. |

(56) References Cited

U.S. PATENT DOCUMENTS

| | | |
|---|---|---|
| 11,665,483 B1 | 5/2023 | Lahoud |
| 11,666,713 B2 | 6/2023 | Lahoud |
| 11,672,928 B2 | 6/2023 | Lahoud |
| 11,690,963 B2 | 7/2023 | Danek |
| 11,730,191 B2 | 8/2023 | Lahoud |
| 11,730,193 B2 | 8/2023 | Lahoud |
| 11,785,985 B2 | 10/2023 | Lahoud |
| 11,796,732 B2 | 10/2023 | Novak et al. |
| 12,066,654 B2 | 8/2024 | Novak et al. |
| 2003/0068277 A1 | 4/2003 | Vanbever et al. |
| 2004/0204354 A1 | 10/2004 | Nelson et al. |
| 2004/0206351 A1 | 10/2004 | McFarland |
| 2005/0011514 A1 | 1/2005 | Power et al. |
| 2007/0267010 A1 | 11/2007 | Fink et al. |
| 2009/0050142 A1 | 2/2009 | Hamano |
| 2009/0095821 A1 | 4/2009 | Feriani |
| 2010/0044460 A1 | 2/2010 | Sauzade |
| 2010/0044480 A1* | 2/2010 | Lindsey .................. B29B 17/02 241/23 |
| 2010/0166673 A1 | 7/2010 | Surber et al. |
| 2010/0260688 A1 | 10/2010 | Warchol et al. |
| 2011/0108025 A1 | 5/2011 | Fink et al. |
| 2011/0117026 A1 | 5/2011 | Tseng et al. |
| 2011/0168194 A1 | 7/2011 | Hon |
| 2011/0226236 A1 | 9/2011 | Buchberger |
| 2011/0265806 A1 | 11/2011 | Alarcon et al. |
| 2012/0236680 A1 | 9/2012 | Panagiotou et al. |
| 2012/0266870 A1 | 10/2012 | Denyer et al. |
| 2013/0056005 A1 | 3/2013 | Knudsen |
| 2013/0058999 A1 | 3/2013 | Foeger |
| 2013/0079732 A1 | 3/2013 | Burt et al. |
| 2013/0119151 A1 | 5/2013 | Moran et al. |
| 2013/0220315 A1 | 8/2013 | Conley et al. |
| 2013/0238723 A1 | 9/2013 | Balannik et al. |
| 2013/0267864 A1 | 10/2013 | Addington |
| 2013/0269684 A1 | 10/2013 | Patton |
| 2014/0007874 A1 | 1/2014 | Ellwanger et al. |
| 2014/0178461 A1 | 6/2014 | Rigas |
| 2015/0165137 A1 | 6/2015 | Mullinger |
| 2015/0223523 A1 | 8/2015 | McCullough |
| 2015/0238723 A1 | 8/2015 | Knudsen |
| 2015/0257447 A1 | 9/2015 | Sullivan |
| 2016/0001019 A1 | 1/2016 | Fink et al. |
| 2016/0050976 A1 | 2/2016 | Righetti |
| 2016/0051582 A1 | 2/2016 | Li et al. |
| 2016/0192708 A1 | 7/2016 | Demeritt |
| 2016/0213866 A1 | 7/2016 | Tan |
| 2016/0228658 A1 | 8/2016 | Minskoff |
| 2016/0338407 A1 | 11/2016 | Kerdemelidis |
| 2016/0374397 A1 | 12/2016 | Jordan et al. |
| 2017/0095002 A1 | 4/2017 | Silvestrini |
| 2017/0119059 A1 | 5/2017 | Zuber et al. |
| 2017/0143627 A1 | 5/2017 | Misra |
| 2017/0172977 A1 | 6/2017 | Kleidon et al. |
| 2017/0273914 A1 | 9/2017 | Knudsen |
| 2017/0281701 A1 | 10/2017 | Kan |
| 2017/0368273 A1 | 12/2017 | Rubin |
| 2018/0043114 A1 | 2/2018 | Bowen et al. |
| 2018/0043115 A1* | 2/2018 | Gould .................. A61M 11/042 |
| 2018/0051002 A1 | 2/2018 | Dull et al. |
| 2018/0146710 A1 | 5/2018 | Bessant et al. |
| 2018/0153217 A1 | 6/2018 | Liu et al. |
| 2018/0161525 A1 | 6/2018 | Liu et al. |
| 2018/0220707 A1 | 8/2018 | Biel et al. |
| 2018/0279667 A1 | 10/2018 | McAdam et al. |
| 2018/0289907 A1 | 10/2018 | Marmur et al. |
| 2018/0296493 A1 | 10/2018 | Kaufman |
| 2018/0360116 A1 | 12/2018 | Schmidt et al. |
| 2019/0008208 A1 | 1/2019 | Cirillo et al. |
| 2019/0014819 A1 | 1/2019 | Sur |
| 2019/0045834 A1 | 2/2019 | Fuisz et al. |
| 2019/0124992 A1 | 5/2019 | Nakano |
| 2019/0150519 A1 | 5/2019 | Liu et al. |
| 2019/0174826 A1 | 6/2019 | Zhu |
| 2019/0183177 A1 | 6/2019 | Hubbard et al. |
| 2019/0247607 A1 | 8/2019 | Knudsen |
| 2019/0282502 A1 | 9/2019 | Boeckl et al. |
| 2019/0289911 A1 | 9/2019 | Liu |
| 2019/0299171 A1 | 10/2019 | Xiong et al. |
| 2019/0364957 A1 | 12/2019 | Fu et al. |
| 2020/0060349 A1 | 2/2020 | Danek |
| 2020/0077704 A1 | 3/2020 | Ouyang |
| 2020/0120989 A1 | 4/2020 | Danek |
| 2020/0154765 A1 | 5/2020 | Lee et al. |
| 2020/0155786 A1 | 5/2020 | Power et al. |
| 2020/0230329 A1 | 7/2020 | Danek |
| 2020/0237007 A1 | 7/2020 | Qiu et al. |
| 2020/0245692 A1 | 8/2020 | Cameron et al. |
| 2020/0261439 A1 | 8/2020 | Pell |
| 2020/0276398 A1 | 9/2020 | Hebrank |
| 2020/0281250 A1 | 9/2020 | Dull et al. |
| 2020/0289770 A1 | 9/2020 | Hebrank |
| 2020/0353186 A1 | 11/2020 | Hebrank et al. |
| 2020/0367553 A1 | 11/2020 | Hejazi |
| 2020/0405995 A1 | 12/2020 | Power et al. |
| 2021/0001381 A1 | 1/2021 | Qiu |
| 2021/0052014 A1 | 2/2021 | Hejazi |
| 2021/0076734 A1 | 3/2021 | Minami et al. |
| 2021/0084970 A1 | 3/2021 | Hejazi et al. |
| 2021/0106772 A1 | 4/2021 | Hebrank |
| 2021/0112882 A1 | 4/2021 | Hejazi |
| 2021/0113783 A1 | 4/2021 | Danek et al. |
| 2021/0121908 A1 | 4/2021 | Sidawi et al. |
| 2021/0177055 A1 | 6/2021 | Lahoud |
| 2021/0178090 A1 | 6/2021 | Lahoud et al. |
| 2021/0195947 A1 | 7/2021 | Lahoud |
| 2021/0212370 A1 | 7/2021 | Moloney et al. |
| 2021/0260312 A1 | 8/2021 | Lacour-Gayet et al. |
| 2021/0275760 A1 | 9/2021 | Hunter |
| 2021/0282465 A1 | 9/2021 | Cristian |
| 2021/0283345 A1 | 9/2021 | Porter et al. |
| 2021/0307376 A1 | 10/2021 | Lahoud et al. |
| 2021/0310913 A1 | 10/2021 | Lahoud et al. |
| 2021/0361889 A1 | 11/2021 | Selby et al. |
| 2021/0402114 A1 | 12/2021 | Lahoud |
| 2021/0404594 A1 | 12/2021 | Hanson et al. |
| 2022/0001121 A1 | 1/2022 | Lahoud |
| 2022/0001122 A1 | 1/2022 | Hunter |
| 2022/0031975 A1 | 2/2022 | Selby et al. |
| 2022/0040418 A1 | 2/2022 | Blick et al. |
| 2022/0040423 A1 | 2/2022 | Marmur |
| 2022/0047818 A1 | 2/2022 | Reinhart et al. |
| 2022/0062565 A1 | 3/2022 | Reinhart et al. |
| 2022/0062942 A1 | 3/2022 | Greenenko et al. |
| 2022/0072182 A1 | 3/2022 | Freeman |
| 2022/0072578 A1 | 3/2022 | Meacham et al. |
| 2022/0080137 A1 | 3/2022 | Hebrank |
| 2022/0105284 A1 | 4/2022 | Lahoud et al. |
| 2022/0110362 A1 | 4/2022 | Lahoud et al. |
| 2022/0132920 A1 | 5/2022 | Danek et al. |
| 2022/0132935 A1 | 5/2022 | Lahoud |
| 2022/0175036 A1 | 6/2022 | Hazani et al. |
| 2022/0218020 A1 | 7/2022 | Lahoud et al. |
| 2022/0218863 A1 | 7/2022 | Edwards et al. |
| 2022/0218921 A1 | 7/2022 | Lahoud et al. |
| 2022/0218922 A1 | 7/2022 | Lahoud et al. |
| 2022/0218923 A1 | 7/2022 | Lahoud et al. |
| 2022/0225664 A1 | 7/2022 | Lahoud et al. |
| 2022/0226587 A1 | 7/2022 | Hunter |
| 2022/0226856 A1 | 7/2022 | Anzenberger et al. |
| 2022/0243289 A1 | 8/2022 | Lahoud et al. |
| 2022/0296823 A1 | 9/2022 | Lahoud et al. |
| 2022/0361564 A1 | 11/2022 | Lahoud et al. |
| 2022/0361565 A1 | 11/2022 | Lahoud et al. |
| 2022/0361567 A1 | 11/2022 | Lahoud et al. |
| 2022/0362490 A1 | 11/2022 | Lahoud et al. |
| 2022/0362494 A1 | 11/2022 | Lahoud et al. |
| 2022/0369698 A1 | 11/2022 | Lahoud et al. |
| 2022/0369699 A1 | 11/2022 | Lahoud et al. |
| 2022/0370737 A1 | 11/2022 | Lahoud et al. |
| 2022/0370739 A1 | 11/2022 | Lahoud |
| 2022/0370740 A1 | 11/2022 | Lahoud et al. |
| 2022/0400745 A1 | 12/2022 | Lahoud |
| 2022/0400746 A1 | 12/2022 | Lahoud |

(56) References Cited

U.S. PATENT DOCUMENTS

| | | |
|---|---|---|
| 2023/0001107 A1 | 1/2023 | Connolly et al. |
| 2023/0028847 A1 | 1/2023 | Lee et al. |
| 2023/0118045 A1 | 4/2023 | Danek et al. |
| 2023/0121005 A1 | 4/2023 | Danek et al. |
| 2023/0166284 A1 | 6/2023 | Aherne et al. |
| 2023/0337735 A1 | 10/2023 | Danek |

FOREIGN PATENT DOCUMENTS

| | | | |
|---|---|---|---|
| CN | 201830669506.0 | | 9/2019 |
| CN | 2020030081539.0 | | 9/2020 |
| EP | 0002234 A1 | | 6/1979 |
| EP | 0718046 A2 | | 6/1996 |
| EP | 1154815 | | 7/2004 |
| EP | 1688146 A1 | | 8/2006 |
| EP | 2886185 A1 | | 6/2015 |
| EP | 2523710 B1 | | 10/2015 |
| EP | 3228345 | | 10/2017 |
| EP | 3298912 A1 | | 3/2018 |
| EP | 3469929 A1 | | 12/2019 |
| FR | 3064490 A1 | | 10/2018 |
| GB | 2524856 A | | 10/2015 |
| GB | 6010917 | | 4/2017 |
| GB | 2570439 A | | 7/2019 |
| KR | 1020100097807 A | | 9/2010 |
| KR | 1020050023256 | | 9/2012 |
| KR | 1020120104964 | | 9/2012 |
| KR | 3020120036331 | | 10/2013 |
| WO | 1993010910 A1 | | 6/1993 |
| WO | 200050111 A1 | | 8/2000 |
| WO | 2013007537 A2 | | 1/2013 |
| WO | 2014167515 A1 | | 10/2014 |
| WO | 2016019353 A1 | | 2/2016 |
| WO | 2016076178 A1 | | 5/2016 |
| WO | 2017076590 A1 | | 5/2017 |
| WO | 2017108394 | | 6/2017 |
| WO | 2017149165 A1 | | 9/2017 |
| WO | 2017183011 A1 | | 10/2017 |
| WO | WO-2017175218 A2 * | 10/2017 | ............. A24F 40/05 |
| WO | 2018002926 A1 | | 1/2018 |
| WO | 2019239217 A1 | | 12/2019 |
| WO | 2020041641 A1 | | 2/2020 |
| WO | 2020081874 A1 | | 4/2020 |
| WO | 2020227717 | | 11/2020 |
| WO | 2021203038 A1 | | 10/2021 |
| WO | 2022/051496 | | 3/2022 |
| WO | 2022/079037 | | 4/2022 |
| WO | 2022/096589 | | 5/2022 |
| WO | 2022/129906 | | 6/2022 |
| WO | 2022/179854 | | 9/2022 |
| WO | 2022/200151 | | 9/2022 |
| WO | 2023111495 A1 | | 6/2023 |
| WO | 2023111496 A1 | | 6/2023 |

OTHER PUBLICATIONS

"Biocompatibility of Medicinal Product Medical Device Combination for Airway Delivery" (Turner), May 17, 2021, retrieved from https://ondrugdelivery.com/biocompatibility-of-medicinal-product-medical-device-combinations-for-airway-delivery.

Uchiyama et al. "Determination of Chemical Compounds Generated from Second-generation E-cigarettes Using a Sorbent Cartridge Followed by a Two-step Elution Method", Analytical Sciences, vol. 32, pp. 549-556, May 2016. (8 pages).

Caly et al., "The FDA-approved drug ivermectin inhibits the replication of SARS-CoV-2 in vitro". Antiviral Research 178 (2020) 104787, www.elsevier.com/locate/antiviral (4 pages).

Farsalinos et al. "Carbonyl Emission in E-cigarette Aerosol: A Systematic Review and Methodological Considerations", Frontiers in Physiology, vol. 8, Article 1119, Jan. 11, 2018, pp. 1-14. (14 pages).

Carugo et al., "Liposome production by microfluidics: potential and limiting factors". Scientific Reports, received: Dec. 15, 2015, accepted: Apr. 22, 2016, Published: May 19, 2016. www.nature.com/scientificreports (15 pages).

Geiss et al. "Correlation of volatile carbonyl yields emitted by e-cigarettes with the temperature of the heating coil and the perceived sensorial quality of the generated vapours", International Journal of Hygiene and Environmental Health, vol. 219, pp. 268-277. (10 pages).

Duell et al., "Nicotine in tobacco products aerosols: It's deja vu all over again". Duell AK, Pankow JF, Peyton DH. Tob Control 2020;29:656-662. <https:// dx. doi. org/ 10. 1136/tobaccocontrol-2019- 055275> (7 pages).

Herrington et al. "Electronic cigarette solutions and resultant aerosol profiles", Journal of Chromatography A, vol. 1418, pp. 192-199, 2015. (8 pages).

Gillman et al. "Effect of variable power levels on the yield of total aerosol mass and formation of aldehydes in ecigarette aerosols", Regulatory Toxicology and Pharmacology, vol. 75, 2016, pp. 58-65. (8 pages).

European patent application 16163666 submitted as priority document in PCT/IL2017/050402, made publicly available by WIPO through publication of the international application on Oct. 12, 2017, 22 pages.

European patent application 16176635 submitted as priority document in PCT/IL2017/050402, made publicly available by WIPO through publication of the international application on Oct. 12, 2017, 31 pages.

European patent application 16187618 submitted as priority document in PCT/IL2017/050402, made publicly available by WIPO through publication of the international application on Oct. 12, 2017, 51 pages.

European patent application 17155046 submitted as priority document in PCT/IL2017/050402, made publicly available by WIPO through publication of the international application on Oct. 12, 2017, 87 pages.

Swain et al. "Excipients and its Variation in Pharmaceutical Aerosol Formulation: A Review", Innovat Internation Journal of Medical & Pharmaceutical Sciences, vol. 1(1), 2016, pp. 4-8. (5 pages).

Green et al. "Pharmaceutical Aerosols—Enhancing the Metered Dose Inhaler", DuPont Central Research & Development. (10 pages).

Klager et al. "Flavoring Chemicals and Aldehydes in E-Cigarette Emissions", Environmental Science & Technology, vol. 51, pp. 10806-10813. (8 pages).

Gardenhire et al., "A Guide to Aerosol Delivery Devices for Respiratory Therapists", American Association for Respiratory Care, 4th Edition, (61 pages).

Wang et al. "A Device-Independent Evaluation of Carbonyl Emission from Heated Electronic Cigarette Solvents", PLOS ONE | DOI: 10.1371/journal.pone.0169811, Jan. 11, 2017, pp. 1-14. (14 pages).

Jensen et al. "Hidden Formaldehyde in E-Cigarette Aerosols", New England Journal of Medicine, Jan. 2015. (7 pages).

Jensen et al. "Hidden Formaldehyde in E-Cigarette Aerosols", Supplementary Appendix, New England Journal of Medicine, Jan. 2015. (3 pages).

"Introducing the G Pen Elite Vaporizer". By GPEN. Dated Mar. 10, 2016, found online [Dec. 8, 2020]. https://.www.gpen.com/blogs/news/112895044-introductin-the-g-pen-elite-vaproizer, Year: 2016, (2 pages).

Borders, Brett, "What is Nanoemulsified CBD?", Aug. 8, 2018, http://brettborders.net/what-is-nanoemulsifiedcbd-oil., Aug. 8, 2018, (9 pages).

Hawkins et al. "Vibrating Mesh Nebulizer Reference Design", Microchip Technology Inc., AN2265. 2016-2017. (50 pages).

"International Search Report" and "Written Opinion of the International Search Authority" (ISA/US) in Respira Technologies, Inc, International Patent Application Serial No. PCT/US2020/056540, dated Feb. 9, 2021 (49 pages).

"International Search Report" and "Written Opinion of the International Search Authority" (ISA/US) in Respira Technologies, Inc, International Patent Application Serial No. PCT/US2020/056541, dated Jan. 12, 2021 (12 pages).

(56) References Cited

OTHER PUBLICATIONS

"International Search Report" and "Written Opinion of the International Search Authority" (ISA/US) in Respira Technologies, Inc, International Patent Application Serial No. PCT/US2021/057477, dated Mar. 16, 2022 (11 pages).
"International Search Report" and "Written Opinion of the International Search Authority" (ISA/US) in Respira Technologies, Inc, International Patent Application Serial No. PCT/US2021/057963, dated Apr. 14, 2022 (10 pages).
Ari. "Jet, Ultrasonic, and Mesh Nebulizers: An Evaluation of Nebulizers for Better Clinical Outcomes", Georgia State University, Respiratory Therapy Faculty Publications, Department of Respiratory Therapy, Eurasian J Pulmonol 2014; 16: 1-7, pp. 1-7. (8 pages).
Weir. "Juul users inhaling chemicals not listed". YaleNews, Jul. 30, 2019. (3 pages).
Rudokas et al. "Liposome Delivery Systems for Inhalation: A Critical Review Highlighting Formulation Issues and Anticancer Applications", Medical Principles and Practice, 2016;25(suppl 2), pp. 60-72, 2016. (13 pages).
Akbarzadeh et al. "Liposome: classification, preparation, and applications", Nanoscale Researh Letters, Nano Review, vol. 8:102. (9 pages).
Vecellio. "The mesh nebuliser: a recent technical innovation for aerosol delivery", Breathe, vol. 2, pp. 252-260, Mar. 2006, (9 pages).
Prichard et al. "Mesh nebulizers have become the first choice for new nebulized pharmaceutical drug developments", Therapeudic Delivery, vol. 9(2), Oct. 17, 2017, pp. 121-136. (16 pages).
Microfluidics "Microfluidizer Processor User Guide. Innovation Through Microfluidizer Processor Technology" Dec. 2014. (10 pages).
Millquist et al., "Inhalation of menthol reduces capsaicin cough sensitivity and influences inspiratory flows in chronic cough." Respiratory Medicine (2013) 107, pp. 433-438, (7 pages).
Naqui et al. "Povidon-iodine solution as SARS-CoV2 prophylaxis for procedures of the upper aerodigestive tract a theroetical framework". Journal of Otolaryngology—Head & Neck Surgery (2020), (4 pages).
Sahiti et al. "Nebulizers: A Review Paper", International Journal of Advanced Research in Computer Science, vol. 8, No.5, May-Jun. 2017 ISSN No. 0976-5697, pp. 1697-1699. (3 pages).
El-Hellani et al. "Nicotine and Carbonyl Emissions From Popular Electronic Cigarette Products: Correlation to Liquid Composition and Design Characteicstics", Nicotine & Tobacco Research, 2018, 215-223 doi: 10.1093/ntr/ntw280/, pp. 216-223. (9 pages).
Omron Mesh Nebulizer Micro AIR U100 (NE-U100-E) Instruction Manual, Nov. 2017. (32 pages).
Philips InnoSpire Go—Portable Mesh Nebulizer, Highlights and Specifications, HH1342/00, version 5.0.1, Dec. 12, 2017. (2 pages).
Respira "Wave" Execs say they Created a Healthier Vape. by Cheddar. Dated Nov. 19, 2019, found online [Dec. 8, 2020]. https://cheddar.com/media/respira-wave-execs-say-they-created-a-healthier-vape Year 2019. (1 page).
"Respira to Submit Nebulizer for FDA Approval.", by tobaccoreporter, dated Jun. 17, 2020, found online [Dec. 8, 2020]. https://tobaccoreporter.com/2020/06/17/respira-to-submit-nebulizer-for-fda-approval/ Year 2020. (2 pages).
Review: Loki Touch Vaporizer, by vaporplants, dated Jan. 12, 2017, found online [Dec. 8, 2020]. https://www.vaporplants.com/review-loki-touch-vaporizer Year 2017. (2 pages).
Rosbrook, K, "Sensory Effects of Menthol and Nicotine in an E-Cigarette" Nicotine & Tobacco Research—Jan. 2016, pp. 1588-1596. https://www.researchgate.net/publication/291206387, (9 pages).
Olszewski et al. "A silicon-based MEMS vibrating mesh nebulizer for inhaled drug delivery", ScienceDirect, Procedia Engineering, vol. 168, pp. 1521-1524. (5 pages).
Stathis et al., "Review of the use of nasal and oral antiseptics during a global pandemic." Future Microbiology (2021) 12(2), pp. 119-130, (12 pages).
"International Search Report" and "Written Opinion" of the International Search Authority (ISA/US) in Respira Technologies, Inc., International Patent Application Serial No. PCT/US2019/047790, dated Nov. 5, 2019 (12 pages).
"International Search Report" and "Written Opinion of the International Searching Authority" (ISA/US) in Respira Technologies, Inc., International Patent Application Serial No. PCT/US2019/056830, mailed Mar. 10, 2020 (12 pages).
"Partial Supplementary European Search Report" (EPO) in Respira Technologies, Inc, European Patent Application Serial No. 19873037.6, dated Aug. 20, 2022 (13 pages).

* cited by examiner

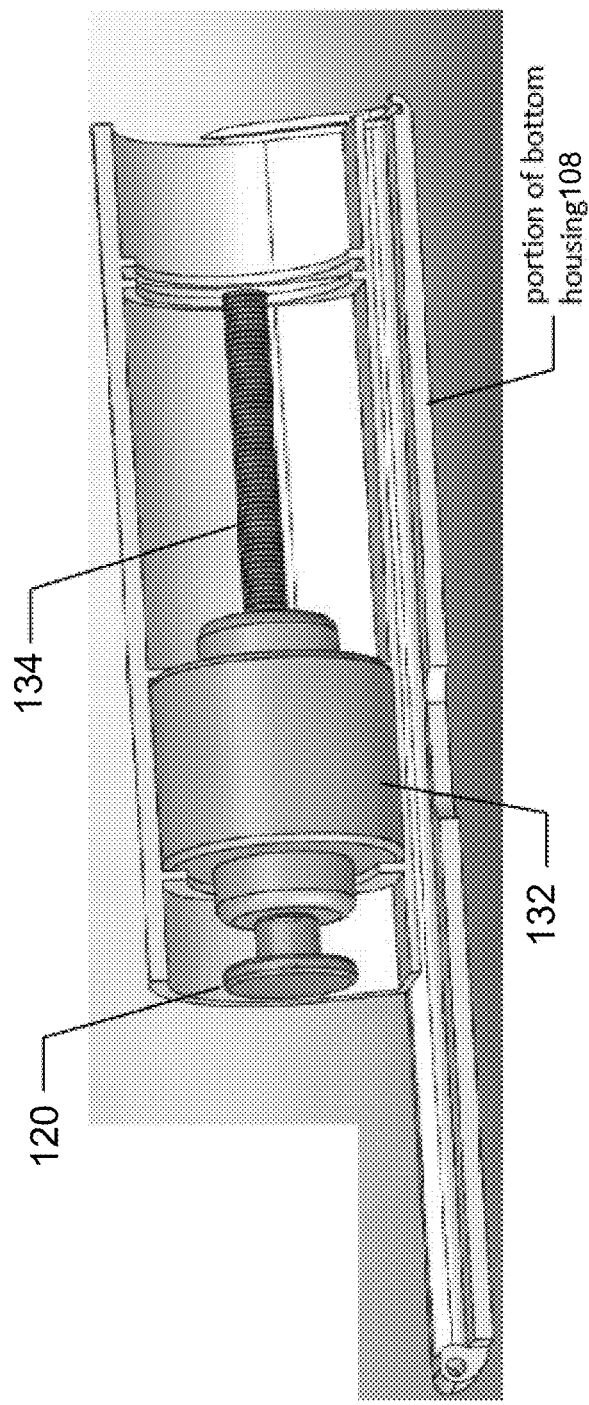

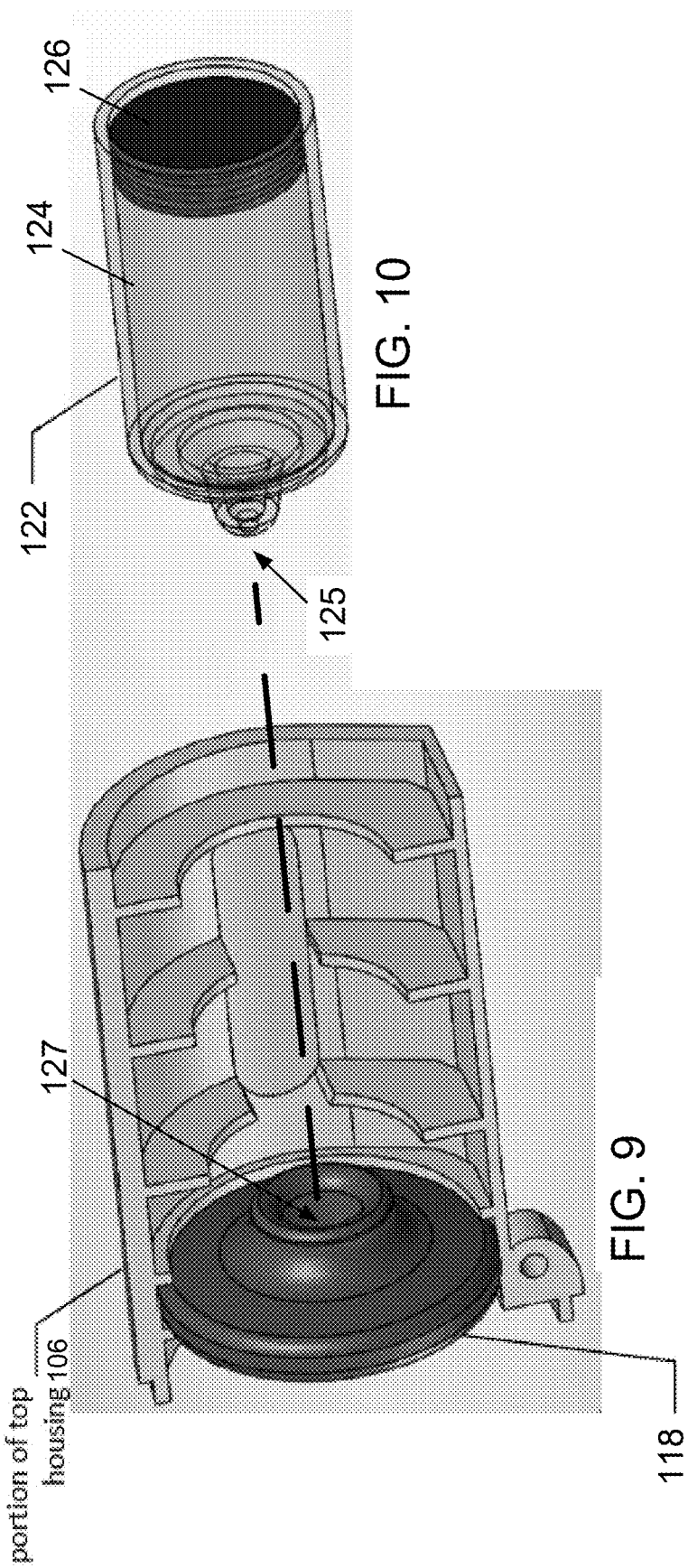

ELECTRONIC DEVICE FOR PRODUCING AN AEROSOL FOR INHALATION BY A PERSON

CROSS-REFERENCE TO RELATED APPLICATION

This application is a U.S. continuation application of, and claims priority under 35 U.S.C. § 120 to, U.S. nonprovisional patent application Ser. No. 16/548,831, filed Aug. 22, 2019, incorporated herein by reference, which '831 application published as U.S. patent application publication 2020/0060338, the disclosure of which is incorporated herein by reference, and which '831 application is a U.S. nonprovisional patent application of, and claims priority under 35 U.S.C. § 119(e) to, U.S. provisional patent application 62/721,310, filed Aug. 22, 2018, the disclosure of which is incorporated herein by reference.

COPYRIGHT STATEMENT

Any new and original work of authorship in this document—including any source code—is subject to copyright protection under the copyright laws of the United States and other countries. Reproduction by anyone of this document as it appears in official governmental records is permitted, but otherwise all other copyright rights whatsoever are reserved.

BACKGROUND OF THE INVENTION

The invention generally relates to apparatus, systems, and methods for producing an aerosol for inhalation by a person, whether intended for personal or recreational use or for the administration of medicines.

Vaping has been rapidly increasing in popularity, primarily because vaping provides a convenient, discreet, and presumably benign way to self-administer nicotine, cannabis, drugs or other micronutrients. Indeed, there is a common belief that vaping is healthier than smoking cigarettes; vaping purportedly lets smokers avoid dangerous chemicals inhaled from regular cigarettes while still getting nicotine. Vaping also can be used for cannabis. Vaping is performed using a vaporizer. A vaporizer includes a vape pen or a cigarette style vape, referred to by many as an e-cigarette or "eCig". A vape pen generally is an elongate, thin, and stylized tube that resembles a fancy pen. In contrast, an e-cigarette resembles an actual cigarette. The e-cigarette is usually small in size (usually smaller and more discreet than vape pens), easily portable, and easy to use. A common vaporizer comprises a liquid container, which may be a tank—which is typically refillable, or a cartridge—which is typically single-use and not refillable. The tank or cartridge holds a liquid often referred to as an e-liquid or e-juice. Tanks are made out of polycarbonate plastic, glass, or stainless steel. The vaporizer also includes a mouthpiece for inhaling by a user through the mouth; an atomizer comprising a tiny heating element that converts the liquid into tiny, airborne droplets that are inhaled; and a controller for turning on the atomizer. Many vape pens turn on automatically when a user inhales. Others require the user to push a button to activate the atomizer. Many vape pins are button activated. Others are mouth-activated. Vaporizers are electrically powered using one or more batteries. The batteries typically are lithium ion batteries that are rechargeable and primarily are used to heat the heating element of the atomizer. A charger usually accompanies a vaporizer when purchased for charging the batteries. The charger may be a USB charger, car charger, or wall charger, and such chargers are generally very similar to phone chargers.

The battery-powered vaporizer produces vapor from any of a variety of substances, especially liquid containing nicotine or cannabinoids, allowing the user to inhale the vapor. Many different types and flavors of liquid are available. Moreover, the liquid can be non-medicated (i.e., containing no nicotine or other substances—just pure vegetable glycerin and flavoring), or the liquid can contain nicotine or even in some instances if and where legal, the liquid can contain THC/CBD. The liquid also may contain one or more of a variety of flavors as well as micronutrients such as, for example, vitamin B12. A user can mix the liquid for use with a vape pen. E-cigarettes typically are purchased with pre-filled cartridges. The heating element turns the contents of the liquid into an aerosol—the vapor—that is inhaled into the lungs and then exhaled by the user. Perhaps one of the most popular vaporizers today is known as the "JUUL", which is a small, sleek device that resembles a computer USB flash drive.

It is believed that while promoted as healthier than traditional cigarette use, vaping actually may be more dangerous. Propylene glycol, vegetable glycerin and combinations or methylations thereof, are chemicals that are often mixed with nicotine, cannabis, or hemp oil for use in vaporizers. Propylene glycol is the primary ingredient in a majority of nicotine-infused e-cigarette solutions. Unfortunately, at high temperatures propylene glycol converts into tiny polymers that can wreak havoc on lung tissue. In particular, scientists know a great deal about propylene glycol. It is found in a plethora of common household items—cosmetics, baby wipes, pharmaceuticals, pet food, antifreeze, etc. The U.S. Food and Drug Administration and Health Canada have deemed propylene glycol safe for human ingestion and topical application. But exposure by inhalation is another matter. Many things are safe to eat but dangerous to breathe. Because of low oral toxicity, propylene glycol is classified by the FDA as "generally recognized as safe" (GRAS) for use as a food additive, but this assessment was based on toxicity studies that did not involve heating and breathing propylene glycol. Indeed, a 2010 study published in the International Journal of Environmental Research and Public Health concluded that airborne propylene glycol circulating indoors can induce or exacerbate asthma, eczema, and many allergic symptoms. Children were said to be particularly sensitive to these airborne toxins. An earlier toxicology review warned that propylene glycol, ubiquitous in hairsprays, could be harmful because aerosol particles lodge deep in the lungs and are not respirable.

Moreover, when propylene glycol is heated, whether by a red-hot metal coil of a heating element of a vaporizer or otherwise, the potential harm from inhalation exposure increases. It is believed that high voltage heat transforms the propylene glycol and other vaping additives into carbonyls. Carbonyls are a group of cancer-causing chemicals that includes formaldehyde, which has been linked to spontaneous abortions and low birth weight. A known thermal breakdown product of propylene glycol, formaldehyde is an International Agency for Research on Cancer group 1 carcinogen!

Prevalent in nicotine e-cig products and present in some vape oil cartridges, FDA-approved flavoring agents pose additional risks when inhaled rather than eaten. The flavoring compounds smooth and creamy (diacetyl and acetyl propionyl) are associated with respiratory illness when inhaled in tobacco e-cigarette devices. Another hazardouswhen-inhaled-but-safe-to-eat flavoring compound is Ceylon cinnamon, which becomes cytotoxic when aerosolized.

When heating element gets red hot in a vaporizer, the liquid undergoes a process called "smoldering", which is a technical term for what is tantamount to "burning"; while much of the liquid is vaporized and atomized, a portion of the liquid undergoes pyrolysis or combustion. In that sense, most of the vaporizers that have flooded the commercial market may not be true vaporizers.

In view of the foregoing, it is believed that a need exists for a vaporizer that provides an aerosol of the desired chemicals without the harmful byproducts that arise from smoldering. This and other needs are believed to be provided by a vaporizer in accordance with one or more aspects and features of the invention.

SUMMARY OF THE INVENTION

The invention includes many aspects and features. Moreover, while many aspects and features relate to, and are described in, the context of vaping, the invention is not limited to use only in such context. Indeed, depending on the context of use, the electronic device of the invention may be considered a vaporizer and may be in the form of a vape pen or e-cigarette. Indeed, those who vape may come to refer to embodiments of the invention as a vape pen even though heat is not utilized to create the aerosol that is inhaled. In the delivery of pharmaceuticals, patients may come to refer to embodiments of the invention as a nebulizer even though compressed gas is not utilized and even though the aerosol that is produced in accordance with the invention may have a smaller particle size than the mist produced by common nebulizers. Other separate and distinct contexts of use of embodiments of the invention may similarly result in different nomenclature of the electronic device. Nonetheless, while the appearance and form factor of embodiments of the invention may vary depending on the context of use, the basic components and operation remain the same.

In an aspect of the invention, an electronic device for producing an aerosol for inhalation by a person comprises: a mouthpiece and an upper housing component to which the mouthpiece attaches, wherein the upper housing component contains a liquid container and a mesh assembly having a mesh material that vibrates when actuated for aerosolizing liquid from the liquid container that comes into contact with the vibrating mesh material, and wherein the aerosol so produced may be inhaled through the mouthpiece; and a lower housing component containing circuitry and a power supply for actuating vibration of the mesh material, wherein electrical pathways connect the mesh assembly of the upper housing component with the circuitry and power supply of the lower housing component.

In a feature, the upper housing component and the lower housing component are detachable from each other, and electrical contacts connect the electrical pathways between the upper housing component and the lower housing component when the upper housing component and the lower housing component are connected.

In a feature, the mouthpiece is detachable from the upper housing component to expose the vibrating mesh material. In this respect, the mouthpiece preferably snaps onto a rim surrounding a recessed area or opening of the upper housing component in which the vibrating mesh material is located, thereby defining a partially enclosed space above the vibrating mesh material.

In a feature, the device comprises no heating element configured to heat the liquid to aerosolize the liquid.

In a feature, the device comprises no compressed gas configured to aerosolize the liquid.

In a feature, the electronic device produces a fine particle, low velocity aerosol for central and deep lung deposition.

In a feature, the mesh assembly comprises an oscillating piezoelectric material that when actuated results in vibrations of the mesh material, which aerosolizes liquid that comes into contact with one side thereof, the aerosol being produced on the opposite side of the vibrating mesh material in the partially enclosed space defined by the mouthpiece when attached to the upper housing component. The oscillating piezoelectric material may be a single layer oscillating piezoelectric material, or the oscillating piezoelectric material may be a multi-layer oscillating piezoelectric material. The oscillating piezoelectric material preferably forms part of a mesh disk.

In a feature, the liquid is pressured into contact with a first side of the vibrating mesh material, and the vibrating mesh material comprises small openings through which droplets of the liquid pass to form the aerosol as the vibrating mesh material oscillates. Furthermore, the droplets of the aerosol produced preferably are between one micron and four microns aerosol droplets.

In a feature, the liquid container comprises a cartridge.

In a feature, the power supply comprises one or more lithium-ion batteries.

In a feature, the power supply comprises one or more rechargeable batteries.

In a feature, the circuitry and power supply are configured to further operate a pump system that causes the liquid from the liquid container to come into contact with the first side of the vibrating mesh material. The pump system preferably comprises a motor and a threaded shaft that is rotated by the motor, the rotation of the threaded shaft causing the liquid to be pushed toward the vibrating mesh material. The liquid preferably is pushed toward the vibrating mesh material by a stopper that is advanced by the rotating shaft; the stopper is advanced by engagement with a plunger that is attached to the threaded shaft and that is directly driven by rotation of the threaded shaft by the motor, or alternatively, the stopper is attached to the threaded shaft and is directly driven by rotation of the threaded shaft by the motor.

In another feature, the electronic device further comprises means for causing the liquid to be in contact with a lower side of the mesh material facing the liquid container. The means may comprise any of the pump systems disclosed herein, whether actively powered or a passive system, such as a capillary pump.

In another feature, the electronic device comprises a capillary pump, wherein the liquid is drawn into contact with the mesh material through capillary action.

In another feature, the upper housing component and the lower housing component fit together to define a body of the electronic device, which body is of a size and shape for gripping and holding by hand during use of the electronic device.

In another aspect, an electronic device for producing an aerosol for inhalation by a person comprises: (a) a mouthpiece; and (b) an elongate housing having opposite first and second ends, with the mouthpiece being attached to the first end and with the housing comprising therein, (i) a mesh assembly comprising a mesh material that vibrates when actuated, (ii) a liquid container containing a liquid that is aerosolized by the mesh material when actuated for inhalation through the mouthpiece, and (iii) circuitry and a power supply for actuating vibration of the mesh material, wherein electrical pathways connect the mesh assembly with the circuitry and power supply; (c) wherein the mesh assembly and the liquid container are arranged in-line along a longitudinal axis of the electronic device.

In a feature, the mesh assembly extends between and separates the mouthpiece and the liquid container.

In a feature, the power supply of the electronic device comprises batteries that are arranged along the longitudinal axis of the device and that are located at the second end of the housing.

In a feature, the liquid contacts the mesh material as a result of capillary action.

In a feature, the electronic device further comprises means for causing the liquid to be in contact with a lower side of the mesh material facing the liquid container.

In another aspect, a method for producing an aerosol for inhalation by a person using an electronic device comprises the steps of causing a mesh material to vibrate while causing a liquid to contact a first side of the mesh material, whereby droplets of the liquid are formed on the opposite side of the mesh material to create an aerosol for inhalation.

In a feature, the mesh assembly comprises a piezo-mesh disk and the liquid is caused to contact the first side of the piezo-mesh disk at a generally constant pressure so that the aerosol that is produced will have a generally consistent concentration of the liquid. Additionally, the liquid preferably is maintained in constant contact with the first side of the piezo-mesh disk, even when not actuated.

Additionally, the electronic device preferably is actuated for a predetermined period of time by a button press, whereby a consistent volume of aerosol for inhalation is produced for each button press. Alternatively, the electronic device is actuated by depressing a button by a user of the electronic device, with the aerosol being produced while the button is depressed. The liquid may be pushed from a cartridge by a stopper that is advanced through a liquid container of the cartridge, and the liquid container of the cartridge may be cylindrical. Furthermore, the stopper may be advanced through the liquid container by actuation of a motor that drives a threaded shaft. This may be accomplished by the stopper being attached to the threaded shaft such that the stopper advances through the liquid container when the threaded shaft is rotated, or by a plunger (or plunger head) being attached to the threaded shaft and advancing through the liquid container when the threaded shaft is rotated such that the plunger engages and advances the stopper for pushing the liquid into contact with the vibrating mesh material.

In another feature, the aerosol preferably is produced without smoldering of the liquid.

In another feature, the aerosol is produced without utilizing a compressed gas.

In another aspect, a method for producing an aerosol for inhalation by a person using an electronic device having a mouthpiece comprises the steps of causing a mesh material to vibrate while causing a liquid to contact a first side of the mesh material, whereby droplets of the liquid are formed on a second, opposite side of the mesh material to create the aerosol for inhalation through the mouthpiece.

In a feature, the device has opposite longitudinal ends and the mouthpiece is located on one of the opposite longitudinal ends of the device.

In a feature, the mesh material has a side facing the mouthpiece and an opposite side facing a liquid container containing the liquid for aerosolized.

In a feature, the mouthpiece, the mesh material, and the liquid container are arranged in-line along the longitudinal axis of the electronic device, with the mesh material extending between and separating the mouthpiece from the liquid container. The mesh assembly in preferred embodiments comprises a piezo-mesh disk.

In a feature, the electronic device is actuated for a predetermined period of time for producing a consistent volume of aerosol for inhalation.

In a feature, the electronic device is actuated by depressing a button by a user of the electronic device.

In a feature, the liquid is caused to contact the first side of the mesh material at a generally constant pressure.

In a feature, the liquid is pushed from a cartridge by a stopper that is advanced through a liquid container of the cartridge. The liquid container of the cartridge preferably is cylindrical but may have another geometric profile. The stopper preferably is advanced through the liquid container by actuation of a motor that drives a shaft. The stopper may be attached to the shaft and directly driven so as to advance through the liquid container when the shaft is rotated, or the electronic device may further comprise a plunger is attached to the shaft and that is directly driven so as to advance through the liquid container when the shaft is rotated, wherein the plunger engages and advances the stopper for pushing the liquid into contact with the vibrating mesh material.

In a feature, the aerosol preferably is produced without smoldering of the liquid.

In a feature, the aerosol preferably is produced without utilizing a compressed gas.

In a feature, the method further comprises a step for causing the fluid to be in constant contact with the mesh material using capillary action. The step may be carried out by an active pump system or a passive pump system such as a capillary pump system using capillary action.

Another aspect comprises using an electronic device in accordance with one or more of the aforementioned aspects and features to perform a method of producing an aerosol for inhalation by a person using such electronic device.

In addition to the aforementioned aspects and features of the invention, it should be noted that the invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the invention now will be described in detail with reference to the accompanying drawings, wherein the same elements are referred to with the same reference numerals.

FIG. 8 is a partial view of components of the electronic device of FIG. 1.

FIG. 9 is another partial view of components of the electronic device of FIG. 1.

FIG. 10 is another transparent view of the cartridge of the electronic device of FIG. 1.

DETAILED DESCRIPTION

Figure 1:
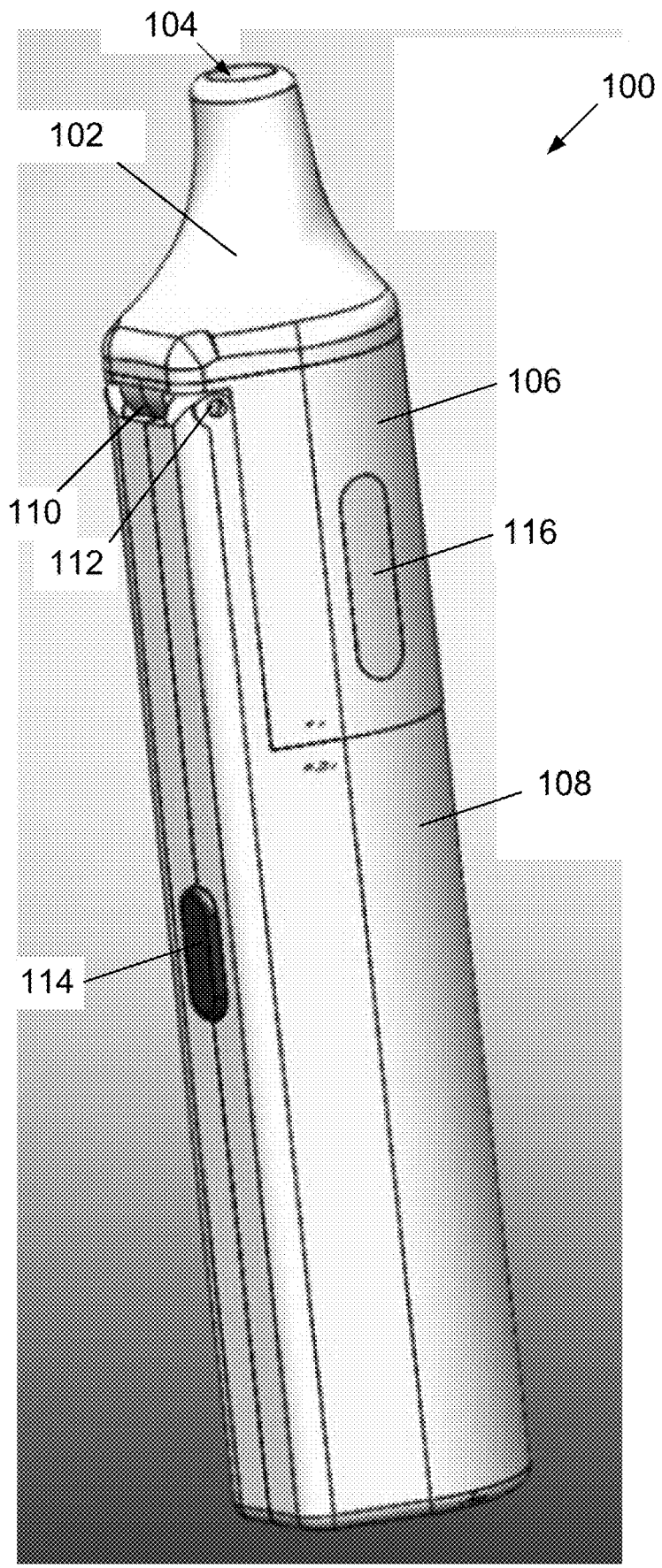
FIG. 1 is a perspective view of a preferred electronic device in accordance with one or more aspects and features of the invention.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Referring now to the drawings, one or more preferred embodiments of the invention are next described. The following description of one or more preferred embodiments is merely exemplary in nature and is in no way intended to limit the invention, its implementations, or uses.

In accordance with electronic devices of the invention, a vibrating mesh is provided for aerosolizing a liquid without smoldering. In the context of vaping, such preferred devices of the invention therefore are believed to produce an aerosol that is carcinogen free. This is in stark contrast to vaporizers used today to aerosolize e-liquids by heating the e-liquids as a way to aerosolize the liquid carrier and desired compounds contained therein (e.g., nicotine) or supplements such as B12, THC/CBD and other drugs or stimulants. As a result of using heating to aerosolize the e-liquids, these vaporizers produce toxic byproducts like formaldehyde, a recognized Group 1 carcinogen for caner, which toxic byproducts then are unfortunately inhaled by a person using the vaporizer. For example, when the liquid carriers are heated, the liquid carriers undergo a thermochemical reaction producing unwanted emissions. The unwanted emissions of the toxic byproducts may cause bodily harm from extended inhalation exposure.

By utilizing a vibrating mesh, preferred electronic devices in accordance with one or more aspects and features of the invention produce an aerosol without using heat and thus advantageously avoid such toxic byproducts created by the vaporizes currently on the market. The electronic devices thereby advantageously produce a carcinogen free aerosol free of harmful emission byproducts.

One of the primary performance metrics evaluated for aerosols is the residual aerodynamic particle size distribution ("APSD") of the aerosolized drug product. The residual APSD is characterized by the residual mass median aerodynamic diameter ("MMAD") and the geometric standard deviation ("GSD"). The MMAD signifies the aerodynamic diameter at which half of the aerosolized drug mass lies below the stated diameter.

The MMADR=MMDI×pI×CNV1/3×pR 1/6, where MMADR (μm) 1 s the mass median aerodynamic diameter of the residual particles, MMDI (μm) is the mass median diameter (MMD) of the initial droplets, CNV (weight fraction) is the concentration of the non-volatile components (e.g., dissolved drug and excipients) in the formulation, and pI and pR are the densities (g/cm3) of the formulation and the residual particles, respectively.

In electronic devices of the invention, the vibrating mesh assembly may include a single layer oscillating piezoelectric material to aerosolize the liquid. In an example, the mesh assembly may have a double or multi-layer structure, and multiple mesh membranes may be arranged to induce an optimum MMAD and/or APSD for the aerosolized liquid.

Additionally, the mesh may be constructed from one or more different piezoelectric materials to optimize the MMAD and/or APSD.

Additionally, the arrangement and design of the mesh assembly (e.g., placement of the holes, angstrom size) and hygroscopic effects of the lungs may be considered for optimum deposition and diffusion into the bloodstream. In an example, the vibrating mesh is configured to create a fine particle low velocity aerosol which is well suited for central and deep lung deposition. By producing a fine particle, low velocity aerosol, one or more preferred electronic devices of the invention advantageously can produce an aerosol that is adapted to target small airways in the management of asthma and COPD.

Additionally, a pump system is utilized to pump or push the liquid to be aerosolized into contact with the vibrating mesh whereby droplets of the liquid are created on the other side of the vibrating mesh on the order of 1 to 4 microns. While it is contemplated that a capillary pump may be used (wherein the liquid is drawn into contact with the mesh material through capillary action), electronic devices of the invention preferably further include a pump system that is powered by an electrical power source of the device, such as batteries and, preferably, rechargeable batteries. Such a pump system preferably comprises a piezoelectric motor, as further described in detail below.

Turning now to the drawings, FIG. 1 is a perspective view of a preferred electronic device 100 for producing an aerosol for inhalation in accordance with one or more aspects and features of the invention. The electronic device 100 comprises a mouthpiece 102 having an opening 104 through which the aerosol is inhaled; an upper housing component 106; and a lower housing component 108. The mouthpiece 102, upper housing component 106, and lower housing component 108 fit together to define a body of the electronic device 100, which body is of a size and shape for gripping and holding by hand during use of the device 100. When used as intended, the electronic device 100 would be held with the mouthpiece 102 oriented upright or at an inclination to horizontal, or any orientation therebetween. Regardless of the orientation, the device 100 works the same in producing the aerosol for inhalation.

The top housing 106 is attached to the lower housing component 108 via a hinge 110 including hinge pin 112 for pivoting movement of the top housing 106 relative to the bottom housing 108 between an open position and a closed position. The closed position is shown, for example, in FIG. 1. The mouthpiece 102 preferably snaps in friction fit onto the top housing 106.

Figure 19:
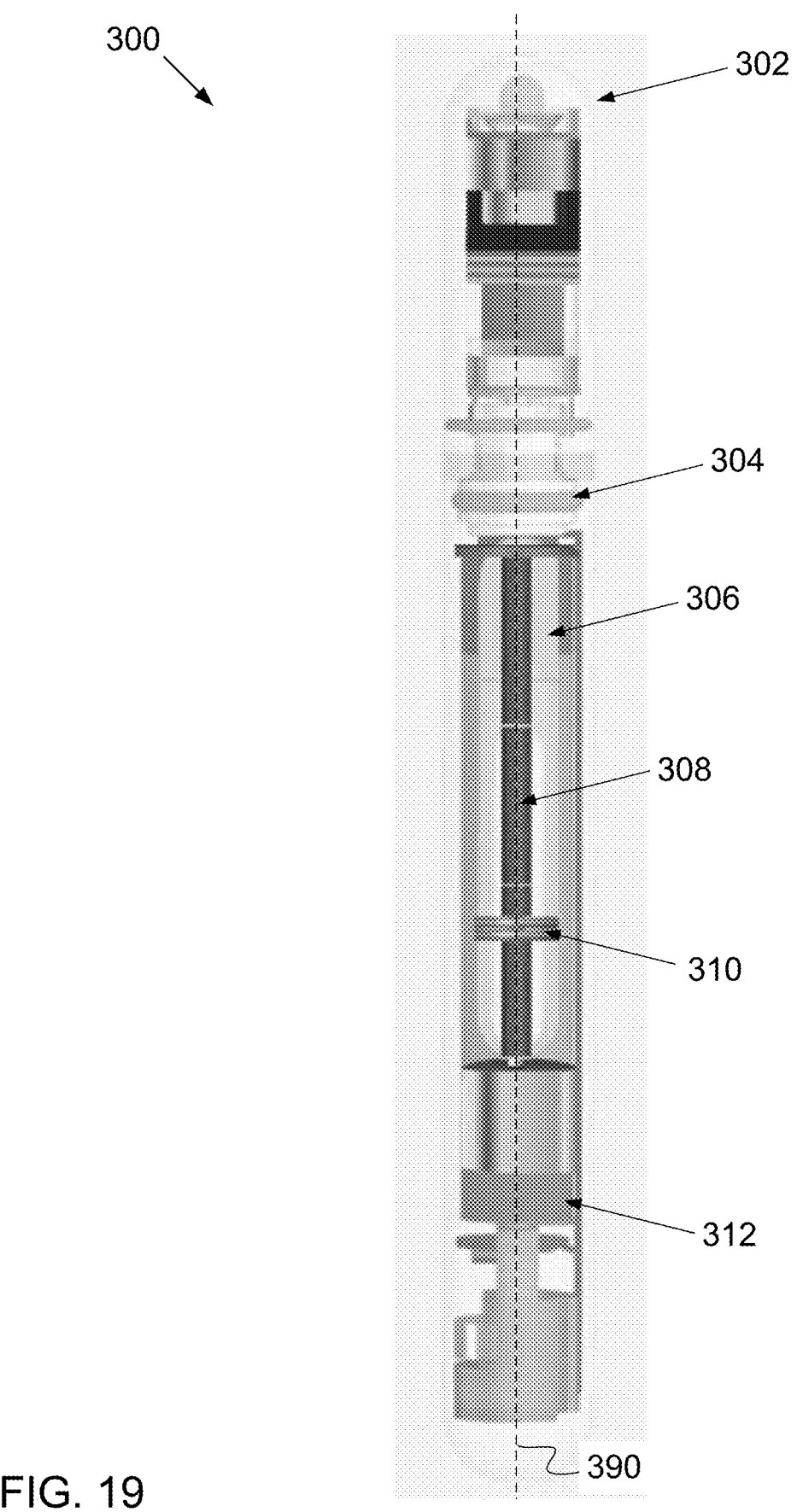
FIG. 19 is a transparent view of internal components of another preferred electronic device in accordance with one or more aspects and features of the invention.

The form factor of the electronic device 100 resembles that of a nebulizer for administering drugs including, for example, prescription medicines. Electronic devices of the invention are not limited to such form factors. For example, another electronic device 300 of the invention is illustrated in FIG. 19, discussed below; electronic device 300 has a form factor resembling that of a vape pen.

Continuing with the description of the electronic device 100, and with further reference to FIG. 1, the device 100 further comprises a button 114 for turning on or otherwise actuating the device 100 and a window 116 for viewing a level of liquid in the device 100. When actuated, the device preferably produces an aerosol for inhalation. A set, predetermined volume of liquid contained in the device preferably is aerosolized each time the device is turned on or actuated using button 114. The amount of liquid remaining in the device to be aerosolized preferably is viewable through the window 116.

Figure 2:
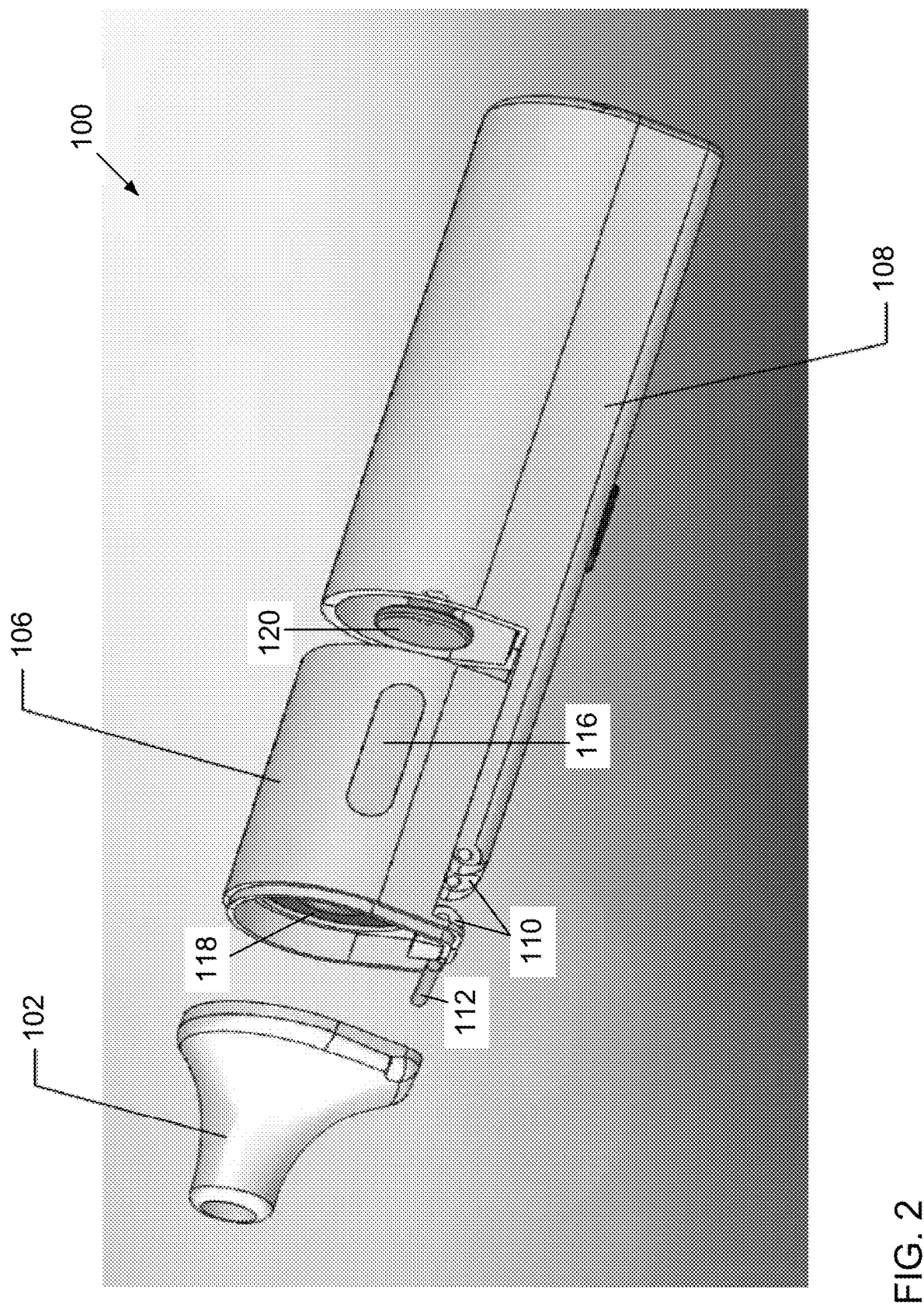
FIG. 2 is an exploded view of components of the electronic device of FIG. 1.

FIG. 2 is an exploded view of components of the electronic device 100. As seen in FIG. 2, the mouthpiece 102, upper housing component 106, and lower housing component 108 are separable from each other. Thus, the body can be disassembled by a user. A glimpse of a mesh assembly 118 including a vibrating mesh in the form of a vibrating mesh material contained within the upper housing component 106 and a glimpse of a plunger 120 contained within the lower housing component 108 also are seen in FIG. 2.

Figure 3:
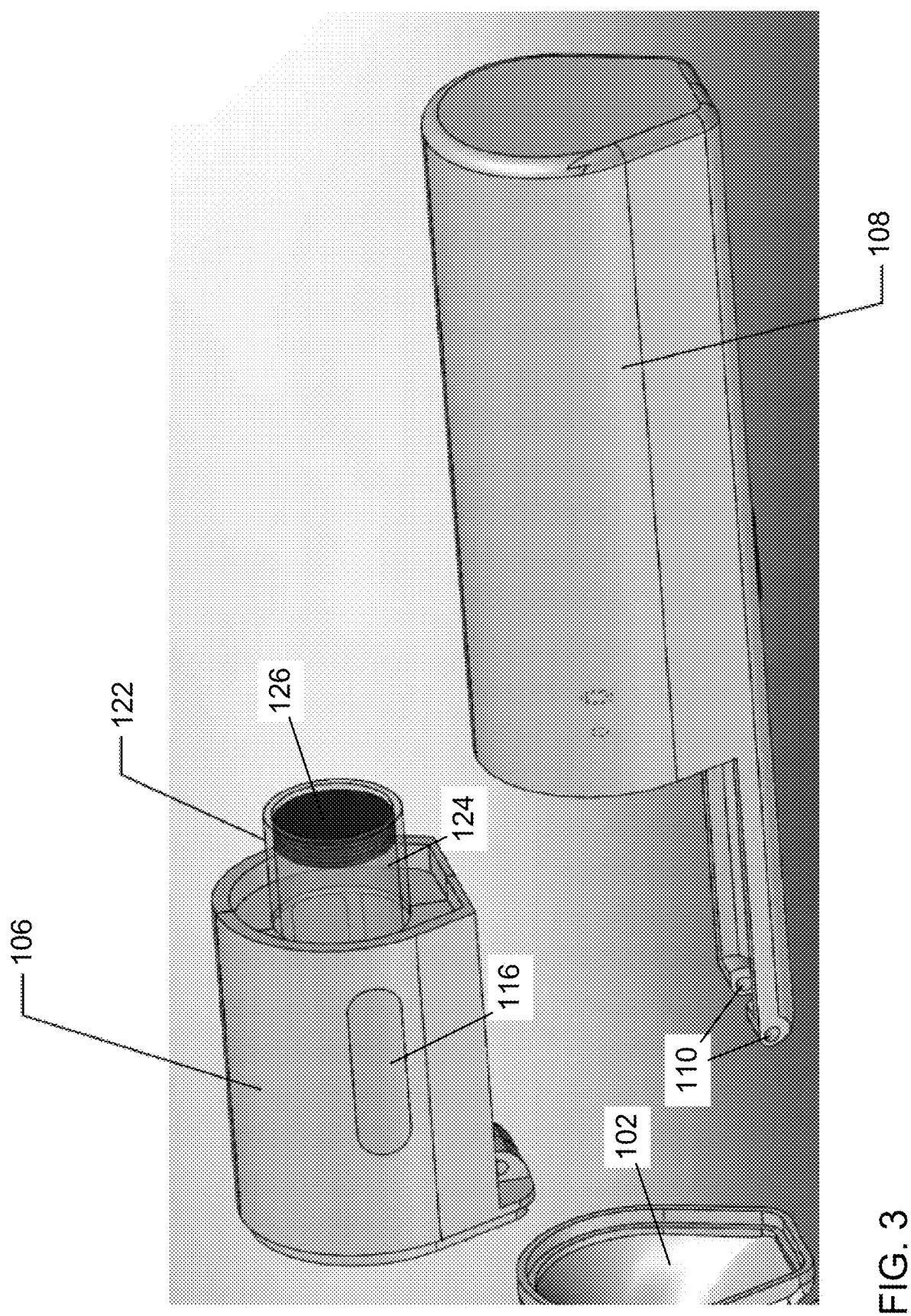
FIG. 3 is another exploded view of components of the electronic device of FIG. 1.

FIG. 3 is another exploded view of components of the electronic device 100. FIG. 3 is perhaps best notable for revealing a liquid container in the form of a cartridge 122 that is contained within the upper housing component 106. The cartridge 122 contains the liquid that is aerosolized and the cartridge 122 preferably is removable from the upper housing component 106 either when the upper housing component is disconnected and separated from the lower housing component 108 or when the upper housing component 106 is rotated from the closed position to an open position by pivoting around the hinge 110 and hinge pin 112. Preferably following use and depletion the cartridge 122 is replaced with a new cartridge having a full supply of liquid to be aerosolized. The cartridge 122 of FIG. 3 is full of a liquid and is seen being inserted into the upper housing component 106. In alternatives, the liquid container may be a tank, i.e., a refillable liquid container that is intended for multiple uses.

As further seen in FIG. 3, the cartridge 122 comprises a cylinder or barrel 124 and a stopper 126. FIG. 3 further reveals that the upper housing component 106 comprises two windows 116 for viewing the volume of liquid contained within the cartridge during use of the device 100.

Figure 4:
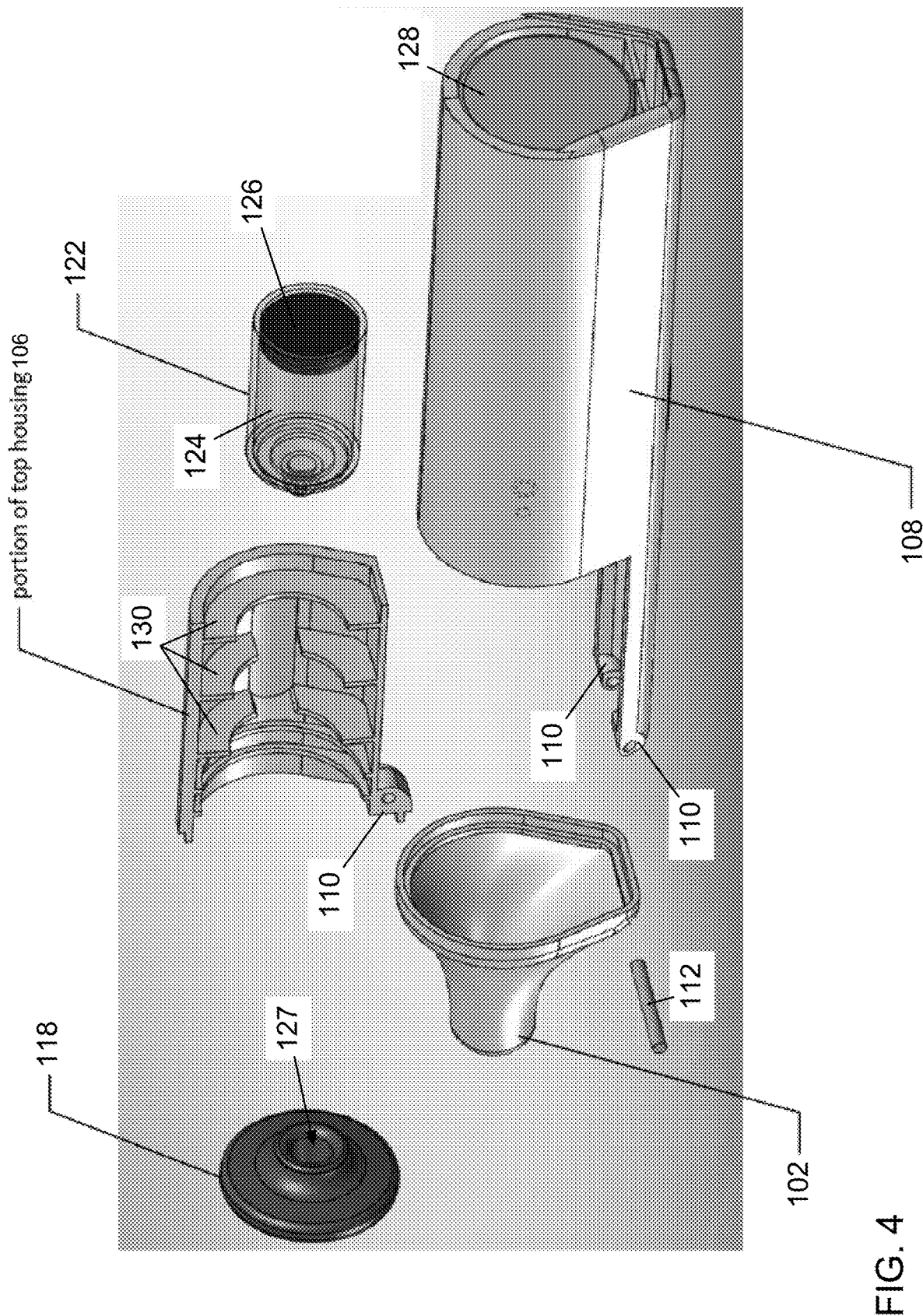
FIG. 4 is a partial, exploded view of components of the electronic device of FIG. 1.

FIG. 4 is a partial, exploded view of components of the electronic device 100. FIG. 4 reveals one or more batteries 128 that are contained within a bottom portion of the lower housing component 108. The batteries preferably are rechargeable lithium-ion batteries. The device 100 preferably includes a charging port 140 (illustrated in FIGS. 11-14) for plugging in a power source for charging the batteries 128. The charging port preferably is a micro-USB charging port. FIG. 4 additionally reveals wall supports 130 of the upper housing component 106 which conform to, receive and support in friction fit the cartridge 122 when inserted into the upper housing component 106. The supports 130 preferably are formed as part of the upper housing component 106, such as during an injection molding process of the upper housing component 106. The lower housing component 108 and mouthpiece 102 also preferably are made by injection molding or other manufacturing methodology.

Similar to supports 130, the upper housing component 106 also comprises wall supports 131 (seen for example in FIG. 5) that hold the mesh assembly 118 in place in the upper housing component 106. Supports 131 also preferably form part of the upper housing component 106 and are similarly formed in a molding process.

Figure 5:
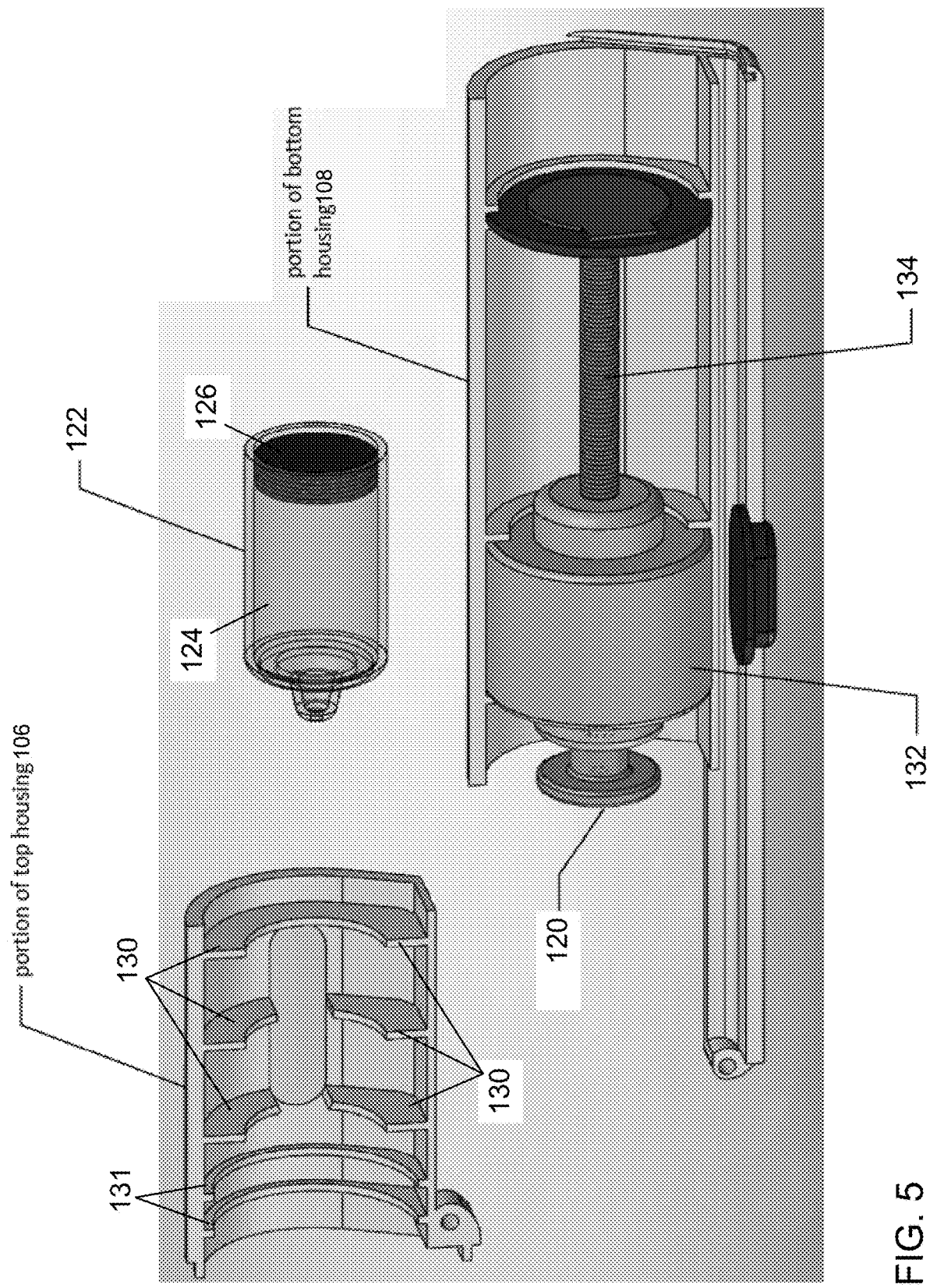
FIG. 5 is another partial exploded view of components of the electronic device of FIG. 1.
Figure 6:
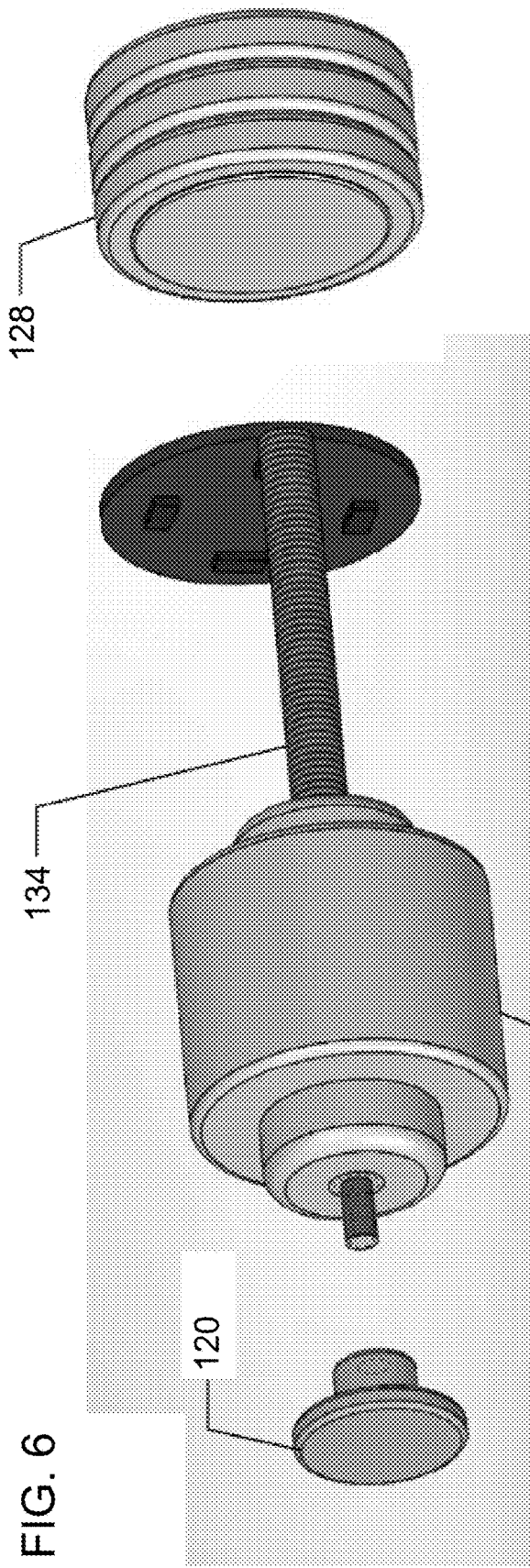
FIG. 6 is another exploded view of components of the electronic device of FIG. 1.

FIGS. 5 and 6 each is another partial, exploded view of components of the electronic device 100 and each reveals a motor 132 and threaded shaft 134. The motor 132 preferably is a piezoelectric motor. The motor 132 drives rotation of the threaded shaft 134 and is actuated by the button 114. The plunger 120 is attached to an end of the shaft 134 and rotation of the shaft 134 by the motor 132 causes the plunger to move in a direction parallel to a longitudinal axis of the rotating shaft 134. FIG. 8 is a partial view of components of the electronic device 100 and additionally shows the plunger 120 attached to the end of the threaded shaft 134 and moved to a fully retracted position in which the plunger 120 is located immediate adjacent the motor 132.

In the device 100, the piezoelectric motor 132 preferably utilizes piezoelectric actuation technology using mechanical waves. The motor advantageously provides a high-power density combined with a high efficiency (e.g., greater than 20 W mechanical) for small motors. In an example, the motor is a purely mechanical structure without any winding. An example suitable motor is the piezoelectric motor WLG-30. The motor may have a stator diameter of approximately 30 mm (1.18 inches), a length of approximately 34 mm (1.34 inches), and a height of approximately 15 mm (0.59 inches). The motor may weight approximately 37 g with an electronic card weight of 23 g. In an example, the motor may have a max speed of approximately 300 rpm with a rated torque of approximately 250 mN·m, a max torque of approximately 50 mN·m, a hold torque of approximately 1 50 mN·m, and a torque resolution of approximately 0.18 mN·m. Additionally, the motor may have an output power of approximately 150 W. The motor response time may be approximately 1.3 milliseconds with a direction change time (CW/CCW) of approximately 1 millisecond and an angular accuracy of approximately 1 degree. In an example, the motor 132 may have a power supply of approximately 7.5V and a max current of approximately 1.2 A.

Figure 7:
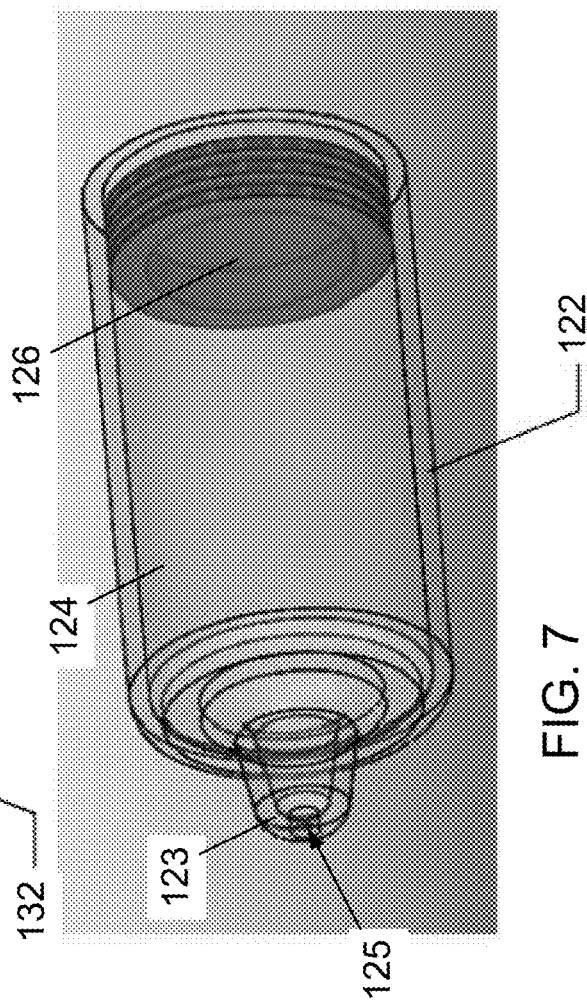
FIG. 7 is a transparent view of components of the electronic device of FIG. 1.
Figure 11:
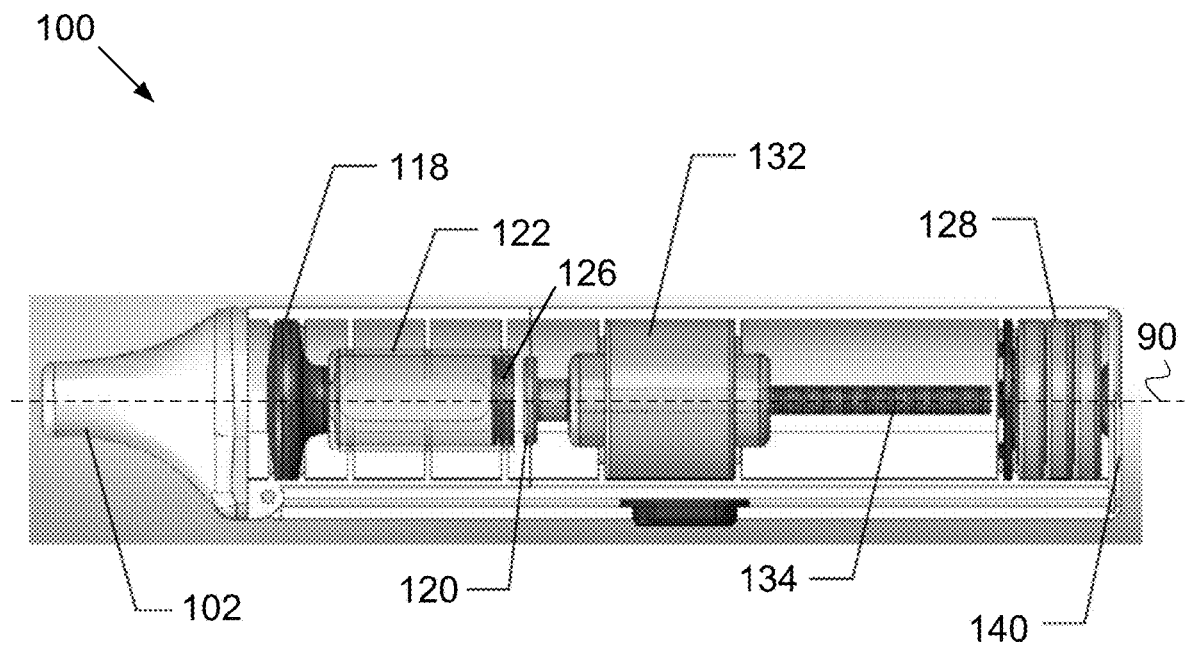
FIGS. 11, 12, 13 and 14 are partial internal views of the electronic device of FIG. 1.
Figure 12:
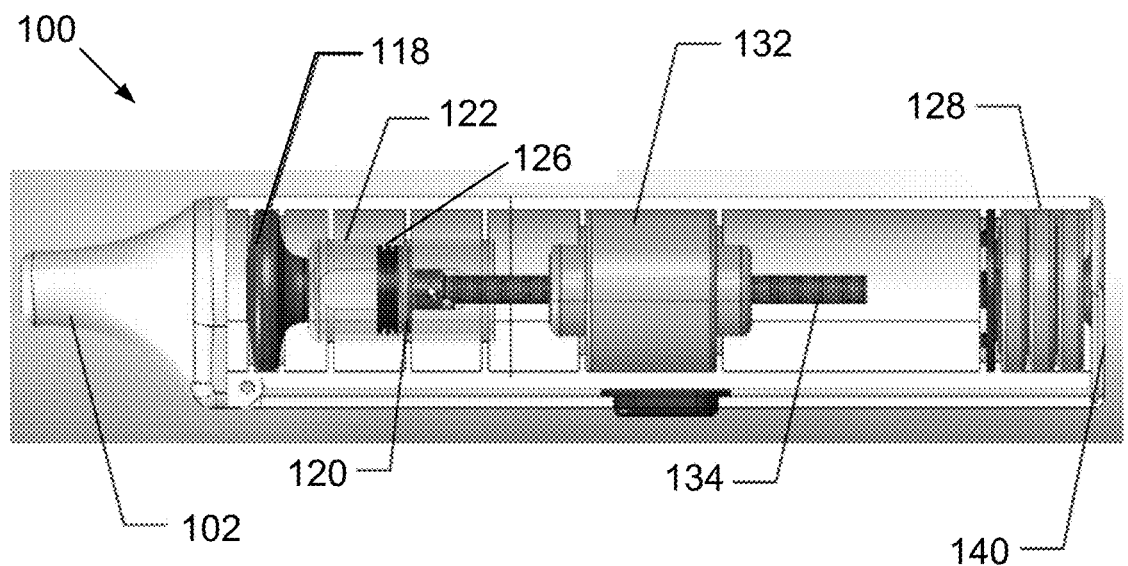

FIG. 7 is a transparent view of the cartridge 122 and components thereof in the electronic device 100. The cartridge 122 is similar to a syringe in that the stopper 126, when advanced within the cylinder 124 toward a tapered end 123 of the cartridge 122, pushes liquid in the cylinder 124 toward the tapered end 123. The stopper 126 forms a seal with the cylinder wall 124 and the stopper 126 prevents or stops the liquid from leaking around the stopper 126.

With reference to FIGS. 9 and 10, the tapered end 123 includes an opening 125 through which the liquid passes when the stopper 126 advances toward the tapered end 123. In particular the tapered end 123 is inserted with the opening 127 when the cartridge 122 is inserted into the upper housing component 106, as indicated by the dashed line extending between FIGS. 9 and 10. Thus, when inserted, the tapered end 123 is located within an opening 127 of the mesh assembly 118 (seen in FIG. 4).

Of course, it will be appreciated that in the electronic device 100 the stopper 126 is not attached to the threaded shaft 134 and, therefore, is not directly driven by rotation of the threaded shaft 134 by the motor 132. Instead, the plunger 120 attached to the end of the threaded shaft 134 is directly driven by rotation of the threaded shaft 134 by the motor 132, which causes the plunger 120 to advance into engagement with the stopper 126 and push the stopper toward the taper end 123. This advancement of the plunger 120 and retraction back is illustrated in the sequence seen in FIGS. 11 through 14, which are partial internal views of the electronic device 100.

It will be appreciated from this sequence of FIGS. 11 through 14 that the components are arranged in-line. In particular, the mouthpiece 102, the mesh assembly 118, and the cartridge 122 containing the fluid are arranged sequentially along a longitudinal axis 90 (seen in FIG. 11) of the device 100 in said order, with the mesh assembly 118 being located between the mouthpiece 102 and the liquid to be aerosolized. The stopper 126, plunger 120, and shaft 134 similarly are arranged along the longitudinal axis 90 of the device 100. Additionally, the motor 132 and batteries 128 also are arranged along the longitudinal axis 90 of the device 100.

Figure 15:
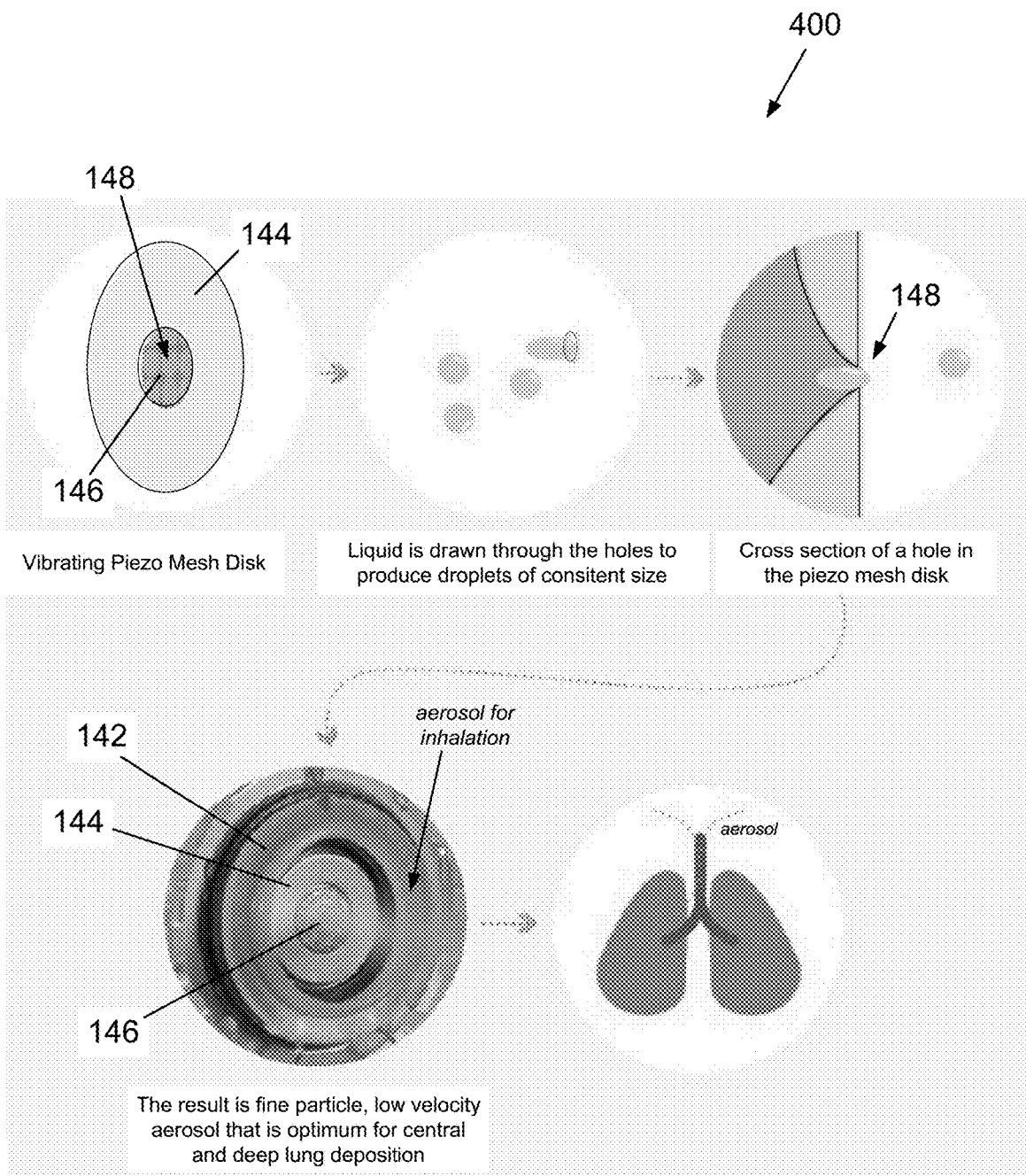
FIG. 15 is a block diagram of a method for producing a fine particle, low velocity aerosol using a preferred electronic device in accordance with one or more aspects and features of the invention.

When the fluid passes through the opening 125 into the opening 127 it contacts a piezo-mesh disk 146 of the mesh assembly 142 (illustrated in FIG. 15). The piezo-mesh disk 146 is held or retained in the mesh assembly 142 by an annular plate 144 similar to a washer. The piezo-mesh disk 146 preferably comprises a piezoelectric material (or "piezo") and has small openings or holes 148 formed therein for the passage of small droplets of the liquid of a consistent size when the piezo-mesh disk 146 is actuated and vibrates. This aerosolizes the liquid producing an aerosol. Preferably the droplets produced are between one-micron and four-micron aerosol droplets.

This sequence 400 of steps is illustrated in FIG. 15. Indeed, FIG. 15 includes a picture of an aerosol for inhalation that is actually produced by the vibrating piezo mesh disk. The aerosol produced by the vibrating mesh is a fine particle, low velocity aerosol that is believed to be optimum for central and deep lung deposition.

Figure 13:
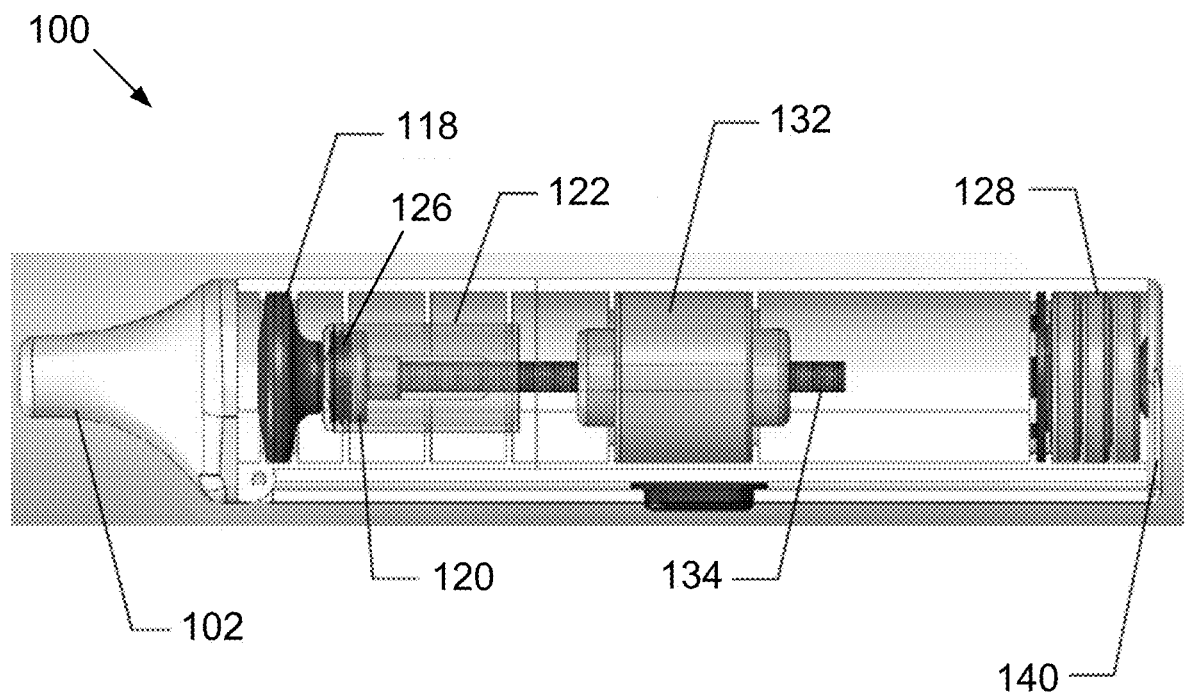
Figure 14:
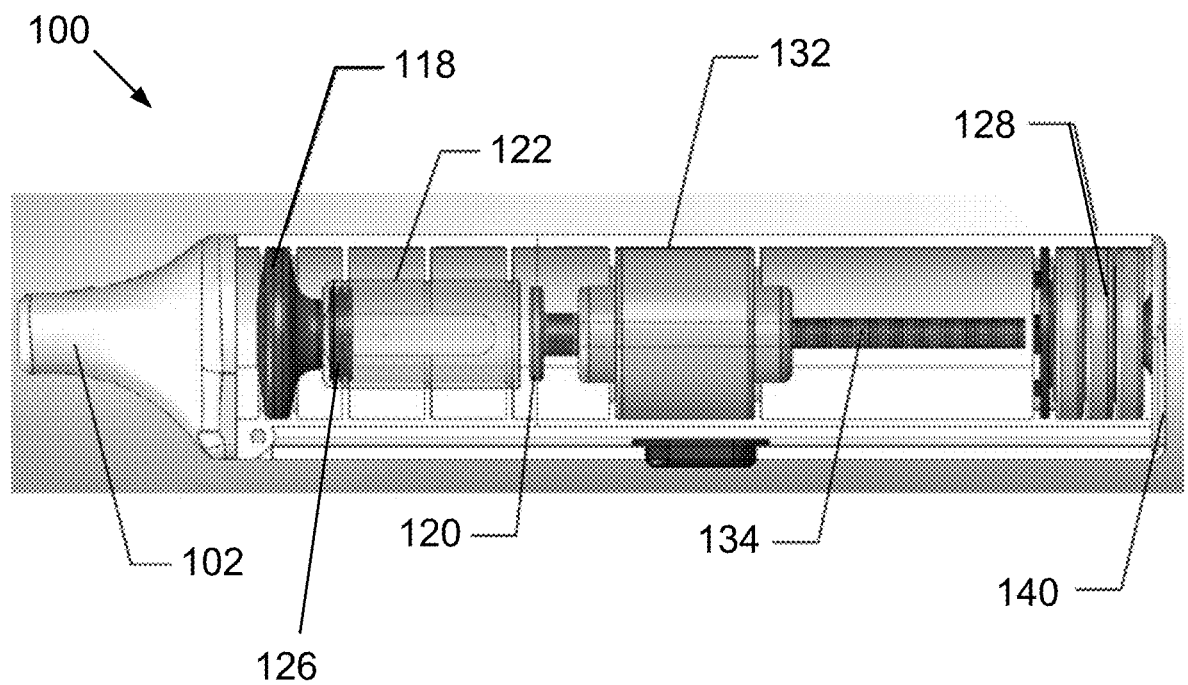

After the plunger 120 has been advanced through the entire cylinder 124 of the cartridge 122 (at which point the cartridge 122 is depleted of the liquid and is empty, as illustrated in FIG. 13), the motor 132 rotates the threaded drive shaft 134 in a reverse direction to return the plunger 120 to the retracted position, as seen in FIG. 14.

Figure 16:
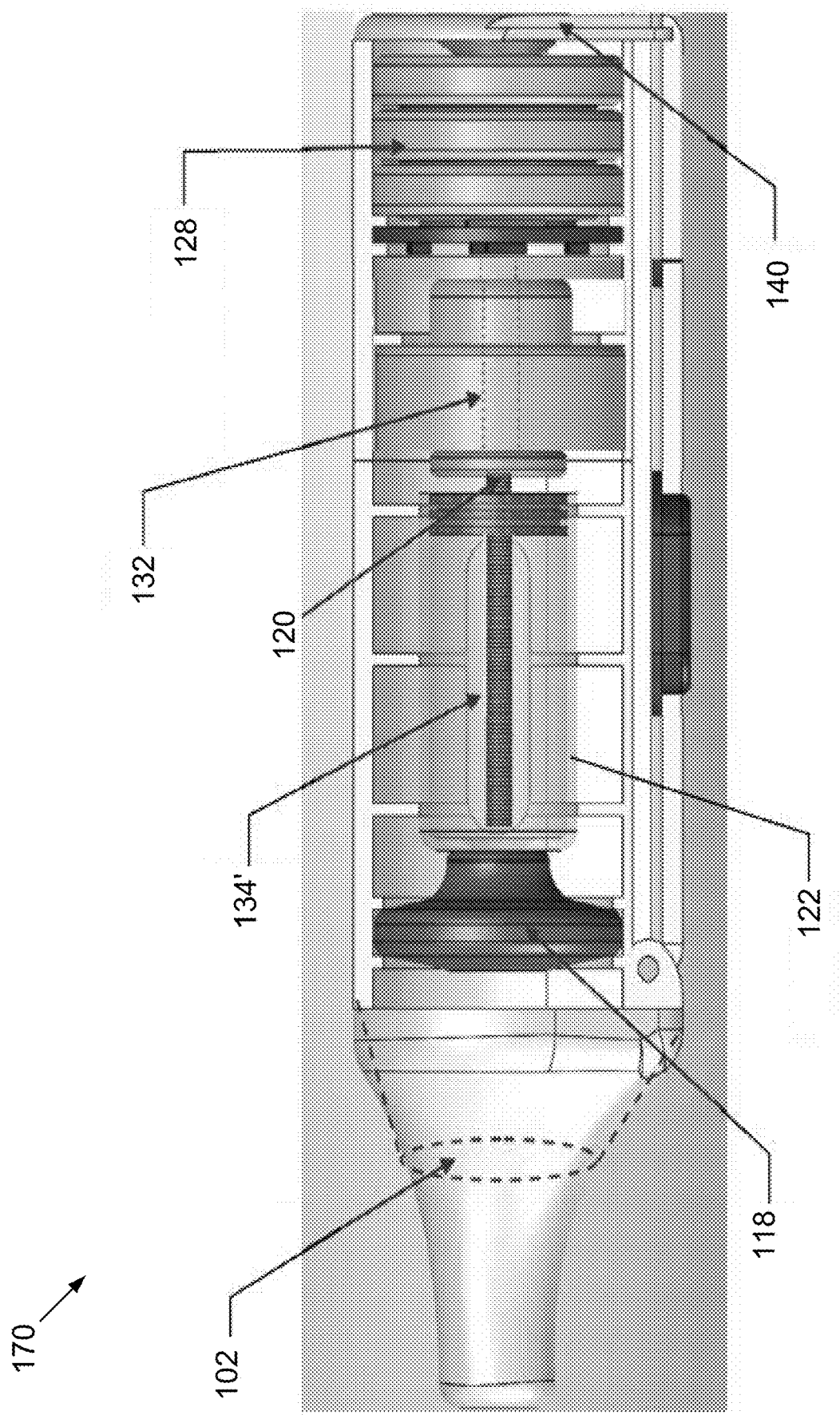
FIG. 16 is a partial internal view of another preferred electronic device in accordance with one or more aspects and features of the invention.

An alternative is illustrated in FIG. 16, which is a partial internal view of another electronic device 170 in accordance with one or more aspects and features of the invention. In this device 170, the cartridge includes the threaded shaft 134' extending therethrough. The other components illustrated and having the same reference numbers as those with respect to device 100 are the same.

Figures 17, 18:
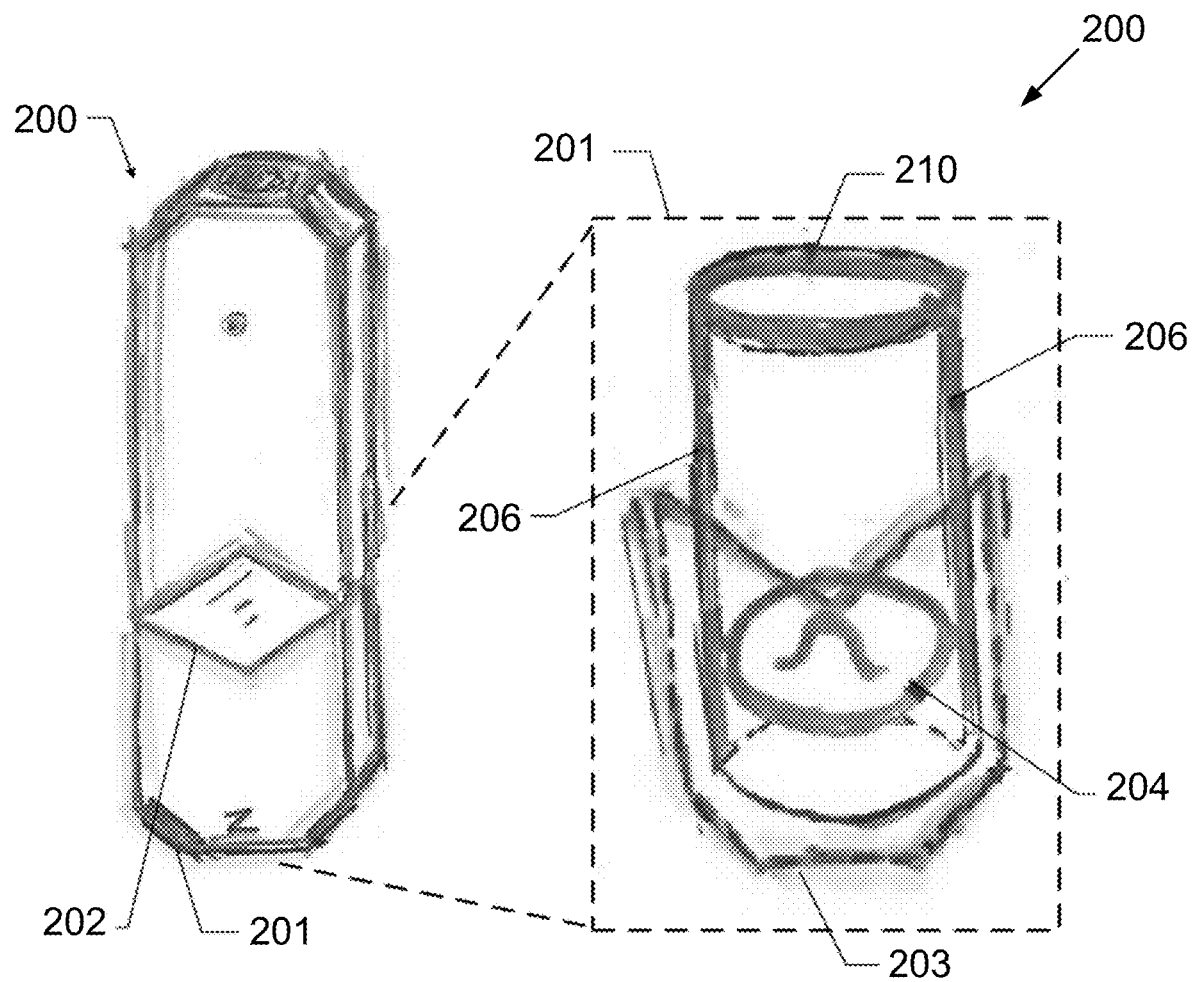
FIG. 17 is a schematic illustration of yet another preferred electronic device in accordance with one or more aspects and features of the invention.
FIG. 18 is a partial schematic illustration of an electromagnetic cartridge of the electronic device of FIG. 17.

Yet another alternative is illustrated schematically in FIGS. 17-18. Specifically, FIG. 17 is a schematic illustration of yet another preferred electronic device 200 in accordance with one or more aspects and features of the invention, and FIG. 18 is a partial schematic illustration of an electromagnetic cartridge of the electronic device 200. Electronic device 200 preferably comprises an electromagnetic propulsion system cartridge (e.g., an electromagnetic syringe pump cartridge 201 having cartridge housing 203) that is utilized to push the liquid into contact with the vibrating mesh when the device 200 is activated. The electronic device 200 includes a liquid window 202. Additionally, the electromagnetic cartridge includes a magnetic stopper 204, an anode 206, a cathode 208, and a magnetic ring 210.

FIG. 19 is a transparent view of internal components of another preferred electronic device 300 in accordance with one or more aspects and features of the invention. The device 300 comprises a number of components that are arranged in-line along a longitudinal axis 390 of the device 300. These components include a mouthpiece 302 from which aerosol produced by the device 300 can be inhaled; a mesh assembly 304 comprising a vibrating mesh and aperture plate; a liquid container 306 comprising a liquid cartridge or reservoir combined with a threaded shaft 308 that longitudinally extends within the liquid container 306 and a stopper 310 that moves longitudinally within the liquid container 306 along the shaft 308 to ensure liquid moves towards and stays in contact with the vibrating mesh; and a motor and battery assembly 312 that drives rotation of the shaft 308 and consequent movement of the stopper 310 within the liquid container 306.

Other contemplated ways of pumping, pushing, or otherwise forcing the liquid into contact with the vibrating mesh include using a solenoid pump, a capillary tube, and a vacuum pump. In each instance regardless of the manner in which the liquid is pushed from the cartridge into contact with the vibrating mesh, the liquid preferably is supplied to the vibrating mesh at a generally constant pressure whereby a generally uniform aerosol is produced. This is preferably done regardless of the orientation of the electronic device. The electronic device also preferably comprises a reservoir for the liquid. In an example, the reservoir is an anti-pyrolysis vape reservoir with no smoldering and no combustion. The device also features a thermostable liquid carrier.

Circuitry (not shown for clarity of illustration) preferably is included in each electronic device for controlling actuation of the vibrating mesh. The circuitry also preferably controls actuation of the pump mechanism for pushing the liquid into contact with the vibrating mesh at a generally constant pressure. A printed circuit board may be included, and an application specific integrated circuit may be included. A microcontroller also may be included (e.g., microchip 8-bit microcontroller-based piezo mesh disk driver board). The microcontroller preferably is located within the lower housing component when included, but in some embodiments the microcontroller may be located within the upper housing component.

Based on the foregoing description, it will be readily understood by those persons skilled in the art that the invention has broad utility and application. Electronic devices of the invention can be utilized to deliver liquids, supplements, drugs, or therapeutically effective amounts of pharmaceuticals using an aerosol having particles of a size that can easily be inhaled. The aerosol can be used, for example, by a patient within the bounds of an inhalation therapy, whereby the liquid, supplement, therapeutically effective pharmaceutical, or drug reaches the patient's respiratory tract upon inhalation. The aerosol also can be used to aerosolize the liquid carrier and desired compounds used in vaping such as nicotine, flavoring, and supplements like B12, without the toxic byproducts like formaldehyde, a recognized Group 1 Carcinogen for caner, which is created when heat traditionally is used to aerosolize the liquid for inhalation. Electronic devices of the invention further can be used in the marijuana industries, but only where legal, for delivery of cannabinoids and CBD oils and the like. Moreover, many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention.

Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof.

What is claimed is:

1. A method of assembling and using an electronic device for producing an aerosol for inhalation by a person, the electronic device comprising three exterior components including a mouthpiece, an upper component, and a hand-held component, the method comprising:
   (a) securing a mesh assembly within the upper component at a distal end of the upper component such that the mesh assembly is exposed at the distal end of the upper component through an opening in the distal end of the upper component, the upper component containing a liquid in contact with the mesh assembly and the mesh assembly having a piezoelectric material and a mesh material that vibrates when the piezoelectric material is actuated for aerosolizing of the liquid;
   (b) attaching a mouthpiece to the distal end of the upper component in opposing facing relation to the mesh assembly such that the mouthpiece defines a partially enclosed space at the distal end of the upper component, the partially enclosed space extending above the mesh assembly, in which partially enclosed space the aerosol is produced when the piezoelectric material is actuated;

(c) bringing together a proximal end of the upper component and
the handheld component, the handheld component containing circuitry and a power supply for actuating the piezoelectric material resulting in vibration of the mesh material,
wherein, when the upper component and the handheld component are brought together, electrical pathways of the upper component and the handheld component connect the mesh assembly of the upper component with the circuitry and power supply of the handheld component;
(d) actuating the piezoelectric material to cause the mesh material to vibrate and aerosolize the liquid in the partially enclosed space defined by the mouthpiece; and
(e) inhaling the aerosol from the partially enclosed space through an opening in the mouthpiece.

2. The method of claim 1, wherein attaching the mouthpiece to the distal end of the upper component comprises snap-fitting the mouthpiece onto the distal end of the upper component.

3. The method of claim 1, wherein the upper component and the handheld component are pivoted relative to each other from an open position to a closed position when the upper component and the handheld component are brought together.

4. The method of claim 1, further comprising exposing the mesh material of the mesh assembly by detaching the mouthpiece from the upper component.

5. The method of claim 1, wherein the mesh assembly comprises a single layer oscillating piezoelectric material.

6. The method of claim 1, wherein the mesh assembly comprises a multi-layer oscillating piezoelectric material.

7. The method of claim 1, wherein the mesh assembly comprises a piezo mesh disk.

8. The method of claim 1, further comprising forcing the liquid into contact with a first side of the vibrating mesh material, wherein the vibrating mesh material comprises small openings through which droplets of the liquid pass to form droplets of the aerosol as the vibrating mesh material oscillates.

9. The method of claim 8, wherein the droplets of the aerosol produced are between one-micron and four-micron aerosol droplets.

10. The method of claim 1, wherein the mouthpiece, the mesh assembly, the upper component, and the handheld component are arranged in-line along a longitudinal axis of the electronic device.

* * * * *